United States Patent [19]
Karn et al.

[11] Patent Number: 6,153,382
[45] Date of Patent: *Nov. 28, 2000

[54] VIRAL GROWTH INHIBITION

[75] Inventors: Jonathan Karn, Little Shelford; Michael John Gait; Shaun Heaphy, both of Cambridge; Colin Dingwall, Cherry Hinton, all of United Kingdom

[73] Assignee: Ribotargets, Ltd., Cambridge, United Kingdom

[ * ] Notice: This patent is subject to a terminal disclaimer.

[21] Appl. No.: 08/929,939

[22] Filed: Sep. 15, 1997

Related U.S. Application Data

[62] Division of application No. 08/540,448, Oct. 10, 1995, Pat. No. 5,786,145, which is a continuation of application No. 08/030,102, filed as application No. PCT/GB91/01616, Sep. 20, 1991, abandoned.

[30] Foreign Application Priority Data

Sep. 20, 1990 [GB] United Kingdom .................. 9020541

[51] Int. Cl.$^7$ ...................................... C12Q 1/68
[52] U.S. Cl. ................................. 435/6; 536/24.1; 514/44
[58] Field of Search ................ 436/6; 536/24.1; 435/6; 514/44

[56] References Cited

U.S. PATENT DOCUMENTS

| | | | |
|---|---|---|---|
| 5,166,195 | 11/1992 | Ecker | ........................................ 514/44 |
| 5,786,145 | 7/1998 | Karn et al. | .................................. 435/6 |

FOREIGN PATENT DOCUMENTS

| | | |
|---|---|---|
| 0 386 563 B1 | 9/1990 | European Pat. Off. . |
| WO91/14436 | 10/1991 | WIPO . |

OTHER PUBLICATIONS

Dingwall, et al., 1989, Human immunodeficiency virus I tat protein binds transactivation–responsive region (TAR) RNA in vitro, *Proc. Natl. Acad. Sci. U.S.A.*, 86 6925–6929.

Feng and Holland, 1988, HIV–1 tat trans–activation requires the loop sequence within tar, *Nature*, 344: 165–167.

Graham and Maio, 1990, RNA transcripts of the human immunodeficiency virus transactivation response element can inhibit action of the viral transactivator, *Proc. Natl. Acad. Sci.*, 87: 5817–5821.

Marciniak, et al., 1990, HIV–1 tat protein trans–activates transcription in vitro, *Cell*, 63: 791–802.

Mitsuya, et al., 1990, Molecular targets for AIDS therapy, *Science*, 249: 1533–1544.

Selby, et al., 1989, Structure, sequence, and position of the stem–loop in tar determine transcriptional elongation by tat through the HIV–1 long terminal repeat, *Genes & Development*, 3: 547–558.

Sullenger, et al., 1990, Overexpression of TAR sequences renders cells resistant to human immunodeficiency virus replication, *Cell*, 63: 601–608.

*Primary Examiner*—Remy Yucel
*Attorney, Agent, or Firm*—Palmer & Dodge, LLP; Kathleen Madden Williams

[57] ABSTRACT

A synthetic molecule comprises at least one oligonucleotide comprising an RNA binding sequence or sequences corresponding to the site bound by the HIV protein rev and capable of binding ot rev within cells. The binding sequence or sequences, by binding with rev within cells, can act to cause inhibition of growth of any HIV present in the cells, and so has potential therapeutic use in treatment of patients infected with HIV. The invention also provides an assay for identifying that inhibit rev binding.

12 Claims, 18 Drawing Sheets

1. Binding of transcription factors to LTR induces basal level transcription of early mRNAs.

2. Tat levels rise and stimulate transcription. Early mRNAs exported from nucleus and translated.
   Late mRNAs retained in nucleus.

3. Rev levels rise and stimulate export of late mRNAs from the nucleus.

(a) Malim et al., 1989

○ Kethoxal
↘ RNase T2
● DEP
↗ RNase CV1

(b) Heaphy et al., 1991

TWJ-C

TWJ-U

RBC2-6X

SEQUENCE LISTING

<160> NUMBER OF SEQ ID NOS: 26

<210> SEQ ID NO 1
<211> LENGTH: 209
<212> TYPE: RNA

<213> ORGANISM: Human immunodeficiency virus

<400> SEQUENCE: 1
ccuuggguuc uugggagcag caggaagcac uaugggcgca gccucaauga cgcugacggu    60
acaggccaga caauuauugu cugguauagu gcagcagcag aacaauuugc ugagggcuau 120
ugaggcgcaa cagcaucugu ugcaacucac agucuggggc aucaagcagc uccaagcaag 180
aguccuagcu guggaaagau accuaaagg 209

<210> SEQ ID NO 2
<211> LENGTH: 66
<212> TYPE: RNA
<213> ORGANISM: Artificial Sequence
<220> FEATURE:
<223> OTHER INFORMATION: Description of Artificial Sequence:Synthetic
RNA derived from HIV RRE sequence

<400> SEQUENCE: 2
gcacuauggg cgcagcguca augacgcuga cgguacaggc cagacaauua uugucuggua 60
uagugc 66

<210> SEQ ID NO 3
<211> LENGTH: 111
<212> TYPE: RNA
<213> ORGANISM: Artificial Sequence
<220> FEATURE:
<223> OTHER INFORMATION: Description of Artificial Sequence:Synthetic
RNA derived from HIV RRE sequence

<400> SEQUENCE: 3
gggagaccgg aauucccuug gguucuuggg agcagcagga agcacuaugg gcgcaguguc 60
auugacgcug acgguacagg ccagacaauu auugucuggu auagugcaac a 111

<210> SEQ ID NO 4
<211> LENGTH: 83
<212> TYPE: RNA
<213> ORGANISM: Artificial Sequence
<220> FEATURE:
<223> OTHER INFORMATION: Description of Artificial Sequence:Synthetic
RNA derived from HIV RRE sequence

<400> SEQUENCE: 4
gggagaccgg aauucagcac uaugggcgca gugucauuga cgcugacggu acaggccaga 60
caauuauugu cugguauagu gca 83

<210> SEQ ID NO 5
<211> LENGTH: 67
<212> TYPE: RNA
<213> ORGANISM: Artificial Sequence
<220> FEATURE:
<223> OTHER INFORMATION: Description of Artificial Sequence:Synthetic
RNA derived from HIV RRE sequence

<400> SEQUENCE: 5
gggagaccgg aauucagcac uagggcgcag ugucauugac gcugagggua caggccagac 60
aauuaua 67

<210> SEQ ID NO 6
<211> LENGTH: 50
<212> TYPE: RNA
<213> ORGANISM: Artificial Sequence
<220> FEATURE:
<223> OTHER INFORMATION: Description of Artificial Sequence:Synthetic RNA derived from HIV RRE sequence

<400> SEQUENCE: 6
gggagaccgg aauucugggc gcagugucau ugacgcugac gguacaggca          50

<210> SEQ ID NO 7
<211> LENGTH: 49
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 7
gggagaccgg aauucugggc gcagugucau ugacgcugcg guacaggca           49

<210> SEQ ID NO 8
<211> LENGTH: 50
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 8
gggagaccgg aauucugggc gcagugucaa ugacgcugac gguacaggca          50

<210> SEQ ID NO 9
<211> LENGTH: 49
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 9
gggagaccgg aauucugggc gcagcgucau ugacacugcg guacaggca           49

<210> SEQ ID NO 10
<211> LENGTH: 36
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 10
gggagaccgg aauucugggc gcuucggcgg uacaga                        36

<210> SEQ ID NO 11
<211> LENGTH: 56
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 11
gggagaccgg aauucugggc gcagugucau ugacgcugcg guacagaauu ccgca    56

<210> SEQ ID NO 12
<211> LENGTH: 56
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 12
gggagaccgg aauucuaaac gcagugucau ugacgcugcg guauagaauu ccggca     56

<210> SEQ ID NO 13
<211> LENGTH: 55
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 13
gggagaccgg aauucuggcg cagugucauu gacgcugcgg uacagaauuc cggca      55

<210> SEQ ID NO 14
<211> LENGTH: 53
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 14
gggagaccgg aauucugggc gcagugucau ugacgcugcg cagaauuccg gca        53

<210> SEQ ID NO 15
<211> LENGTH: 53
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 15
gggagaccgg aauucugcgc agugucauug acgcugcggu acagaauucc ggc        53

<210> SEQ ID NO 16
<211> LENGTH: 10
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 16
ugugggcgca                                                        10

<210> SEQ ID NO 17
<211> LENGTH: 10
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 17
ugcgguacac                                                        10

<210> SEQ ID NO 18
<211> LENGTH: 12
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence -continued

```
<400> SEQUENCE: 18 guguggggcgc ag                                                           12

<210> SEQ ID NO 19
<211> LENGTH: 12
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 19
cugcgguaca ca                                                            12

<210> SEQ ID NO 20
<211> LENGTH: 14
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 20 cguguggcg cagc                                                           14

<210> SEQ ID NO 21
<211> LENGTH: 15
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 21
gcugcgguac acacg                                                         15

<210> SEQ ID NO 22
<211> LENGTH: 16
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 22
gcacuauggg cgcagc                                                        16

<210> SEQ ID NO 23
<211> LENGTH: 18
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 23
gcugcgguac aggccaga                                                      18

<210> SEQ ID NO 24
<211> LENGTH: 13
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 24
```

```
ucuggcauag ugc                                                              13

<210> SEQ ID NO 25
<211> LENGTH: 13
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 25
ucugguauag ugc                                                              13

<210> SEQ ID NO 26
<211> LENGTH: 15
<212> TYPE: RNA
<213> ORGANISM: Artificial Sequence
<220> FEATURE:
<223> OTHER INFORMATION: Description of Artificial Sequence:Synthetic
      RNA derived from HIV RRE sequence

<400> SEQUENCE: 26
gggagaccgg aauuc                                                            15
```

VIRAL GROWTH INHIBITION

This is a divisional application Ser. No. 08/540,448, filed Oct. 10, 1995, now U.S. Pat. No. 5,786,145, which is a continuation of U.S. Ser. No. 08/030,102, filed Mar. 18, 1993, now abandoned, which is a national phase filing of PCT/GB91/01616, filed Sep. 20, 1991, which is a PCT filing of GB9020541.0, filed Sep. 20, 1990.

FIELD OF THE INVENTION

This invention relates to a method of and compositions for use in the inhibition of viral growth within cells. Specifically, the invention relates to the inhibition of growth of the human immunodeficiency virus (HIV).

BACKGROUND TO THE INVENTION

The HIV genome is tightly compressed (FIG. 1). At least 30 different RNA transcripts are produced by splicing using the six splice acceptors and two splice donor sequences [see references 85, 86]. The structural proteins encoded by HIV are chemically similar to those of the C-type retroviruses and like them are encoded as polyproteins by the gap (group antigen), pol (polymerase) and env (envelope) genes. Cleavage of the polyproteins by the viral protease or cellular enzymes generates eight functional virion proteins. In addition to these structural genes, HIV-1 also caries genes for three regulatory proteins, rev (regulator factor); and two proteins involved in virus maturation, vif (virion infectivity factor) and vpu (viral protein U). The vpr (viral protein R) gene encodes a low copy number virion component. In the closely related viruses HIV-2 and simian immunodeficiency virus (SIV) vpr is replaced by vpx (viral protein X), a unique virion protein.

Transcription of the HIV genome during virus replication shows distinct kinetic phases (see references 53,59,60,79). The initial products of HIV gene expression are short, multiply spliced mRNAs approximately 1.8 to 2.0 kb in length, which encode the trans-acting regulatory proteins tat,rev (and possibly nef). As infection by the virus develops, and the levels of the tat and rev proteins rise in the infected cells, mRNA production shifts progressively towards production of a family of singly-spliced 4.3 kb mRNAs encoding env and other HIV gene products such as vif and vpr. Finally, late in the infection process, production switches to full-length, unspliced, transcripts which act both as the virion RNA and the mRNA for the gag-pol polyprotein.

To achieve this control of gene expression, the HIV virus relies on the interaction of cellular and virus-encoded trans-acting factors with cis-acting viral regulatory sequences (1,3,53). Initiation of transcription relies largely on the presence of binding sites for cellular transcription factors in the viral long terminal repeat (LTR) (28). In contrast, the virally encoded regulatory proteins tat and rev exert their activity via cis-acting sequences encoded within HIV messenger RNAs. The trans-activation-responsive region (TAR) is required for tat activity, and is located in the viral long terminal repeat (LTR) between residues +1 and +79 (5,9, 10,11,12,13,14,16,27,38). In rev minus cells only the short spliced transcripts appear in the cytoplasm. It therefore seemed likely that a regulatory sequence was present in one of regions removed form regulatory gene mRNAs by splicing. After a systematic search, a cis-acting sequence required for rev activity, was mapped to a complicated RNA stem-loop structure located within the env rading frame. This sequence has been named the rev-responsive element (RRE). The rev-responsive element (RRE) has been localized to a 234-nucleotide long sequence within the env gene (47,51,54,65,67,68,77). Similar regulatory proteins and target sequences are used by HIV-2 and SIV (8,66). The HTLV-1 virus rex gene product appears to function analogously to rev, and can functionally substitute for rev to promote viral gene expression (76).

The distinct kinetic phases of HIV transcription are now believed to reflect the intracellular levels of the regulatory proteins tat and rev. Initially, binding of host transcription factors to the LTR induced basal level transcription of the early mRNAs including tat. As tat levels rise, increased transcription from the LTR is stimulated by the trans-activation mechanism. This leads to further increases in tat levels, and also stimulates production of rev. Production of the viral sturctural proteins begins once rev levels have risen to sufficiently high levels to promode export of messenger RNAs carrying the rev-responsive element (RRE) sequence. The HIV growth cycle may also include a latent stage where viral gene expression is silent because transcription from the viral LTR produces insufficient amounts of regulatory proteins to initiate the lytic growth cycle.

Becuase the rev protein acts post-transcriptionally to mediate the shift towards expression of the late, largely unspliced viral mRNAs (53,60,78,79), rev protein was initially proposed to be a resulator of splicing in HIV. Subsequent work has shown that expression of rev protein permits the appearance in the cytoplasm of transcripts carrying RRE sequences. In the absence of rev, mRNAs carrying the RRE sequence are retained in the nucleus (52,54,65). Although mRNA presursors carrying heterologous splice donor or acceptor sequences may become rev-responsive by addition of the intact RRE sequences (65), it is still unclear whether the effects of the rev protein are coupled to splicing itself or if a still undefined pathway regulates the export of mRNA from the nucleus. In vitro, the rates of splicing of strong splice donor and acceptor sequences, such as from the globin gene, appear to be insensitive to the presence of RRE sequences, suggesting that rev function competes with the splicing function (46).

Rev recognition of the RRE, like tat recognition of TAR, is due to direct binding [33,34,47,68,73,84]. Binding is tight ($K_d$=1–3 nM) and highly specific for the RRE [33, 34,84]. However, the binding behaviour of rev to RRE RNA is much more complex than the binding of tat to TAR RNA. As the concentration of rev increases, progressively larger complexes with RRE RNA are formed, whereas tat only forms one-to-one complexes with TAR RNA.

The simplest explanation for the RNA binding behaviour of rev is that the protein binds initially to a high affinity site and that subsequently additional rev molecules occupy lower affinity sites [33]. We have recently mapped the high affinity rev binding site to a purine-rich "bubble" located near the 5' end of the RRE [87]. Mutations that disrupt or delete the "bubble" abolish RRE activity [51,68]. The low affinity binding reaction is the result of both protein-protein and protein-RNA interactions. At high concentrations rev polymerizes and forms long filaments 14 nm wide and up to 1,500 nm long. Because of its ability to polymerize, when rev is mixed with HIV mRNAs the RNA is packaged into rod-like ribonucleoprotein filaments. Filament assembly appears to be nucleated by the binding of rev to the RRE and is much more efficient on RNA molecules carrying a functional RRE sequence than on molecules that do not include an RRE sequence than on molecules that do not inlcude an RRE sequence [87].

The RNA binding properties of rev have led us to propose that rev blocks splicing simply by packaging unspliced RNA transcripts containing the RRE sequence into inaccessible ribonucleoprotein complexes [87]. Although complexes containing rev and viral mRNAs have not yet been isolated from infected cells, there is already indirect evidence in support of this type of mechanism. For example, it is believed that the blocking of splicing in vitro by rev is due to the disruption of spliceosome assembly [46]. Furthermore, the in vivo activity of rev appears to be highly concentration dependent, as would be expected for a mechanism of action based on RNA packaging. Rev-minus viruses can only be rescued by co-transfection with very high levels of rev-expressing plasmids [88].

The packaging model also provides a simple kinetic explanation for the delayed appearance of the virion RNA and physical explanation for how rev can act on RREs placed in a wide variety of positions. During HIV infection high levels of the 4.3 kb mRNAs, such as the env mRNA, are synthesized for several hours before significant levels of the full-length virion RNA is produced [59]. Compared to the 4.3 kb mRNAs, the virion RNA carries additioknal unused splice donor and acceptor towards its 5' end, far away from the RRE where filament formation is suggested to nucleate. If stabilization of the virion RNA requires production of a longer ribonucleoprotein filament than the stabilization of the 4.3 kb mRNAs, it is easy to imagine that this would only take place late in the infectious cycle, when intracellular rev protein concentrations are expected to be maximal.

Although we believe tha the physical properties of rev can alone account for its biological activity, there have been some reports that cellular co-factors(s) are also required [89]. Trono and Baltimore suggested that a human cell contains a species-specific factor required for rev activity after observing that mouse cells infected by HIV have a rev-minus phenotype which can be easily reversed by fusion to human cells [89]. However, it is possible that rev protein levels differed between the various cell lines, and that only sub-threshold levels of rev were expressed in the mouse cells [89]. By contrast, rev is functional in *Drosophila melanogaster* cells [90].

It is an aim of the present invention to provide an effective method for, and compositions for use in, the inhibition of HIV viral growth within cells, which involves modifying the activity of the regulatory protein rev in the viral growth cycle, and also an assay for screening potential anti-viral agents.

STATEMENT OF THE INVENTION

According to a first aspect of the present invention there is provided a synthetic molecule comprising at least one oligonucleotide comprising an RNA binding sequence or sequences corresponding to the site bound by the HIV protein rev and capable of binding to rev within cells.

The binding sequence or sequences, by binding rev within cells, can act to cause inhibition of the growth of any HIV present in the cells, and so has potential therapeutic use in treatment of patients infected with HIV.

According to a second aspect of the present invention, there is provided a pharmaceutical composition comprising a molecule as provided by the first aspect of the invention. The pharmaceutical composition is conveniently for use as an inhibitor of growth of HIV within cells.

According to a third aspect of the invention, there is provided a synthetic molecule for use in treating patients infected with HIV, the molecule comprising at least one oligonucleotide comprising an RNA binding sequence or sequences corresponding to the binding site bound by the HIV protein rev and capable of binding to rev within cells.

According to a fourth aspect of the invention, there is provided the use of a molecule as provided by the first aspect of the invention, in the manufacture of a medicament for inhibiting growth of HIV within cells.

The present invention is based around the unexpected discovery that only a small and specific region of the RRE sequence is critical for binding rev protein. It is therefore reasonably practicable to synthesise (chemically or enzymatically) pharmaceutically acceptable nucleic acid or other analogues of this specific binding site, which are sufficiently small to be capable of assimilation into cells.

These analogues can then be used as inhibitors of rev protein activity in cells; by binding to rev present in the cells the analogues are able to block its reaction with the RRE present on viral transcripts and thus viral growth in those cells could be effectively inhibited.

It has been found that transcripts corresponding to RRE residues 26–96, 33–96, and 26–66 bind rev with the same affinity as the full-length 223 nucleotide transcript. However, transcript 37–96 has no discernible affinity for rev. Therefore the rev binding sequence maps to between nucleotides 33 at the 5' end and 66 at the 3' end. Thus, the maximum size of the rev binding site is 34 nucleotides and this corresponds to a predicted stem-loop structure which is necessary (and may be sufficient) for rev binding and RRE function in vivo. It has further been found that rev recognizes a specific purine rich "bubble" formed by these stem-loop structures. Placement of the "bubble" in other non-homologous stem loop structures confers specificity for rev binding. Chemically synthesized analogues of the rev binding site, containing the purine-rich "bubble" structure are also able to bind rev spefically and to compete effectively with the full-length RRE sequence.

Hence, the binding sequence in the oligonucleotide of the present invention preferably comprises a sequence of non-Watson-Crick-base-paired residues corresponding to those in the HIV-1 RRE fragments which form this "bubble" structure.

Because such a small region of the RRE is actually needed to bind rev, analogues of the binding site can be constructed which are composed of oligonucleotides of therapeutically useful lengths, preferably (but not limited to) twenty residues or less. Such molecules are more likely to be able to enter infected cells, and hence to be of use in pharmaceuticals for in vivo treatment of HIV infections, than are those of greater length. A molecule in accordance with the invention is thus preferably in the form of an oligonucleotide(s) less than or equal to twenty residues in length, so as to facilitate assimilation into cells infected with HIV.

Since RNA itself is metabolically unstable in cells, the oligonucleotide(s) used in of the present invention is preferably modified in some way so as to increase its stability in the cells. The binding sequence, which is necessarily an RNA sequence, may for instance be incorporated into a DNA basic sequence or some other structurally-related variant oligonucleotide, which basic sequence imparts the necessary metabolic stability to the oligonucleotide(s) as a whole.

Thus any oligonucleotide (or combination of oligonucleotides) which includes the RNA sequence corresponding to the site bound by rev, when introduced into cells, should be capable of binding rev and thus acting as a competitive inhibitor of viral growth within those cells. Indeed, any small molecule which is able to bind to rev at the RRE RNA binding site could be used as an anti-viral agent, and the invention includes within its scope such a molecule for use as an anti-HIV agent. Such a molecule could mimic the shape of the RNA structure in RRE RNA or could contain functional groups equivalent to the RNA structure in RRE RNA.

Since oligoribonucleotides are sensitive to cleavage by cellular ribonucleases, it may be preferable to use as the competitive inhibitor a chemically modified oligonucleotide (or combination of oligonucleotides) that mimics the action of the RNA binding sequence but is less sensitive to nuclease cleavage. Other modifications may also be required, for example to enhance binding, to enhance cellular uptake, to improve pharmacology or pharmacokinetics or to improve other pharmaceutically desirable characteristics.

The oligonucleotide may be a naturally occuring oligonucleotide, or may be a structurally related variant of such an oligonucleotide having modified bases and/or sugars and/or linkages. The term "oligonucleotide" as used herein is intended to cover all such variants.

Modifications, which may be made either to the binding site per se or to the part of the oligonucleotide not involved in binding, may include (but are not limited to) the following types:
a) Backbone modifications (see FIG. 4 below)
  i) phosphorothioates (X and Y or W or Z=S or any combination of two or more with the remainder as 0). e.g. Y=S (81), X=S (49), Y and Z=S (45)
  ii) methylphosphonates (eg Z=methyl (69))
  iii) phosphoramidates (Z=N-(alkyl)$_2$ e.g. alkyl=methyl, ethyl, butyl) (Z=morpholine or piperazine) (44) (X or W=NH) (64)
  iv) phosphotriesters (Z=O-alkyl e.g. methyl, ethyl etc) (70)
  v) phosphorus-free linkages (e.g. carbamate, acetamidate, acetate) (55,56)
b) Sugar modifications
  i) 2'-deoxynucleosides (R=H)
  ii) 2'-O-methylated nucleosides (R=OMe) (80)
  iii) 2'-fluoro-2'-deoxynucleosides (R=F) (61)
c) Base modifications—(for a review see 58)
  i) pyrimidine derivatives substituted in the 5-position (e.g. methyl, bromo, fluoro etc) or replacing a carbonyl group by an amino group (75).
  ii) purine derivatives lacking specific mitrogen atoms (eg 7-deaza adenine, hypoxanthine) or functionalised in the 8-position (e.g. 8-azido adenine, 8-bromo adenine)
d) Oligonucleotides covalently linked to reactive functional groups, e.g.:
  i) psoralens (71), phenanthrolines (82), mustards (83) (irreversible cross-linking agents with or without the need for co-reagents)
  ii) acridine (intercalating agents) (57)
  iii) thiol derivatives (reversible disulphide formation with proteins) (48)
  iv) aldehydes (Schiff's base formation)
  v) azido, bromo groups (UV cross-linking)
  vi) ellipticenes (photolytic cross-linking) (74)
e) Oligonucleotides covalently linked to lipophilic groups or other reagents capable of improving uptake by cells, e.g.:
  i) cholesterol (63), polyamines (62), other soluble polymers (e.g. polyethylene glycol)
f) Oligonucleotides containing alpha-nucleosides (72)
g) Combinations of modifications a)-f)

It should be noted that such modified oligonucleotides, while sharing features with oligonucleotides designed as "anti-sense" inhibitors, are distinct in that the compounds correspond to sense-strand sequences and the mechanism of action depends on protein-nucleic acid interactions and does not depend upon interactions with nucleic acid sequences.

The molecule and the pharmaceutical composition of the present invention may be administered orally, intravenously or by any other suitable method when used to inhibit viral growth in vivo. They may also be used to inhibit viral growth in vitro, for instance in cells in blood which has been removed from a living organism and is later required for transfusion purposes.

The present invention further provides a method of inhibiting growth of HIV virus within cells, comprising the step of administering to the cells a molecule or pharmaceutical composition in accordance with the invention.

The invention also provides a method of treatment of a patient infected with HIV, comprising the step of administering to the patient a molecule or pharmaceutical composition in accordance with the invention.

The invention can also be used as the basis of an assay for identifying compounds that inhibit binding of rev protein to RRE RNA or synthetic analogs thereof, and so have potential use as anti-viral agents.

Thus in a further aspect the invention provides an assay for identifying compounds that inhibit binding of rev protein to RRE RNA, comprising reacting a compound with rev protein and a molecule in accordance with the invention, and determining the degree of binding of rev to the molecule.

By determining the degree of binding of rev to the molecule, and comparing this with results for known standards, an indication can be obtained of the degree of inhibition (competitive or non-competitive) of rev/RRE binding caused by the compound.

The assay is preferably in the form of a filter binding assay, but may also be another type of assay such as a gel mobility-shift assay, a spectroscopic assay, capture assay etc.

Accurate measurement of the affinity of rev for RRE RNA in the presence of inhibitor molecules, such as competitor molecules that compete for binding to RRE or molecules that inhibit rev binding to RRE non-competitively, cannot be achieved without the formation of stoichiometric complexes between tat protein and RRE RNA, which is now possible in vitro as a result of improvements in the purification of rev protein from *E. coli* and in methods for performing binding assays.

Compounds identified as having an inhibitory effect on rev/RRE binding can then be further investigated for possible use as an anti-viral agent. The invention can thus enable screening of potential anti-viral compounds.

The present invention will now be described in greater detail, by way of illustration, with reference to the accompanying Figures, of which:

FIG. 4a shows the predicted secondary structure of the rev-response element RNA as given incorrently by Malim et al. (65) while FIG. 4b shows the correct structure predicted using the program of Zuker. The Figure also indicates sites of enzymatic cleavage and chemical modification as determined by Kjems et al. (92);

Figure 10:
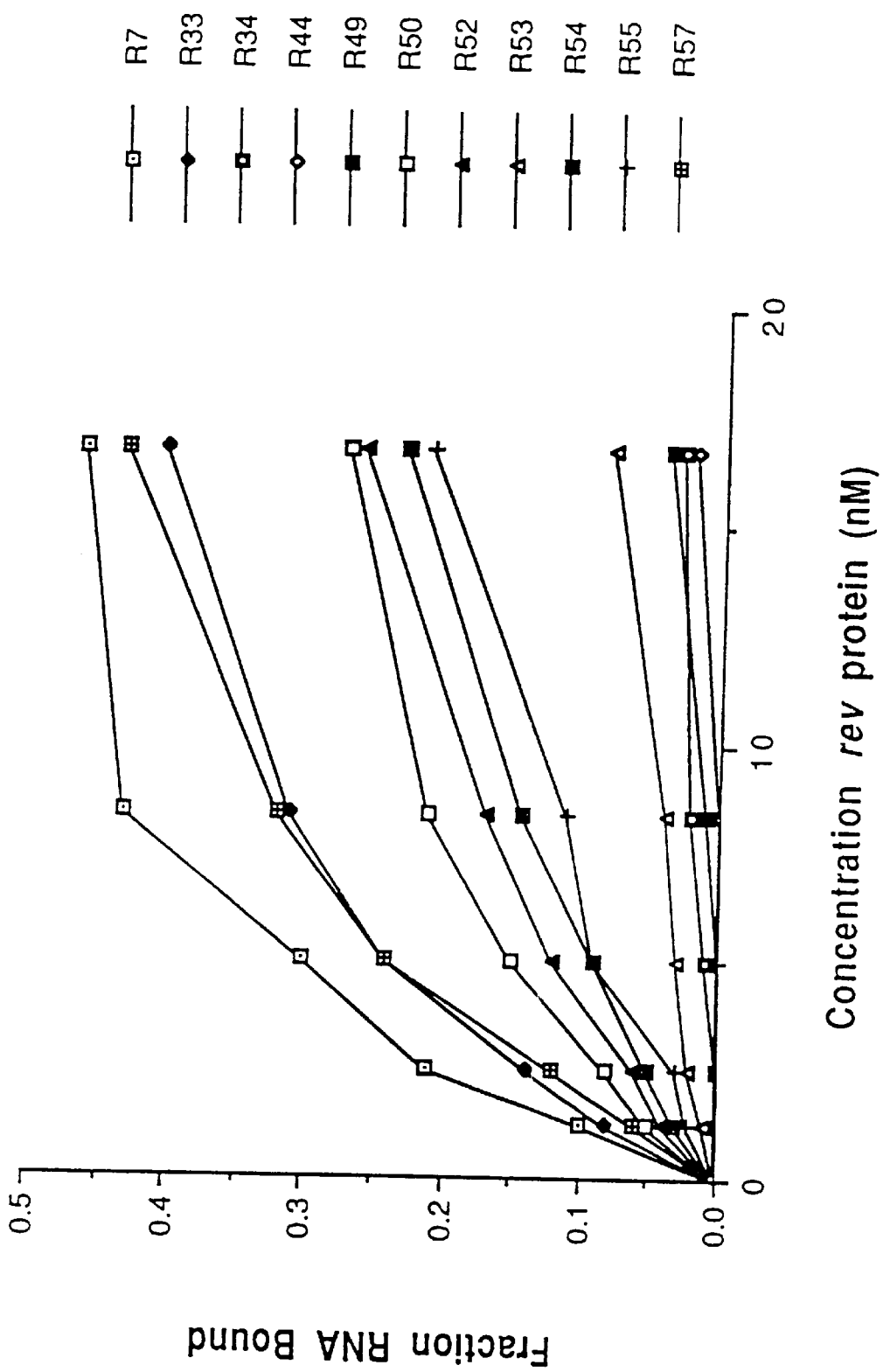
Figure 11:
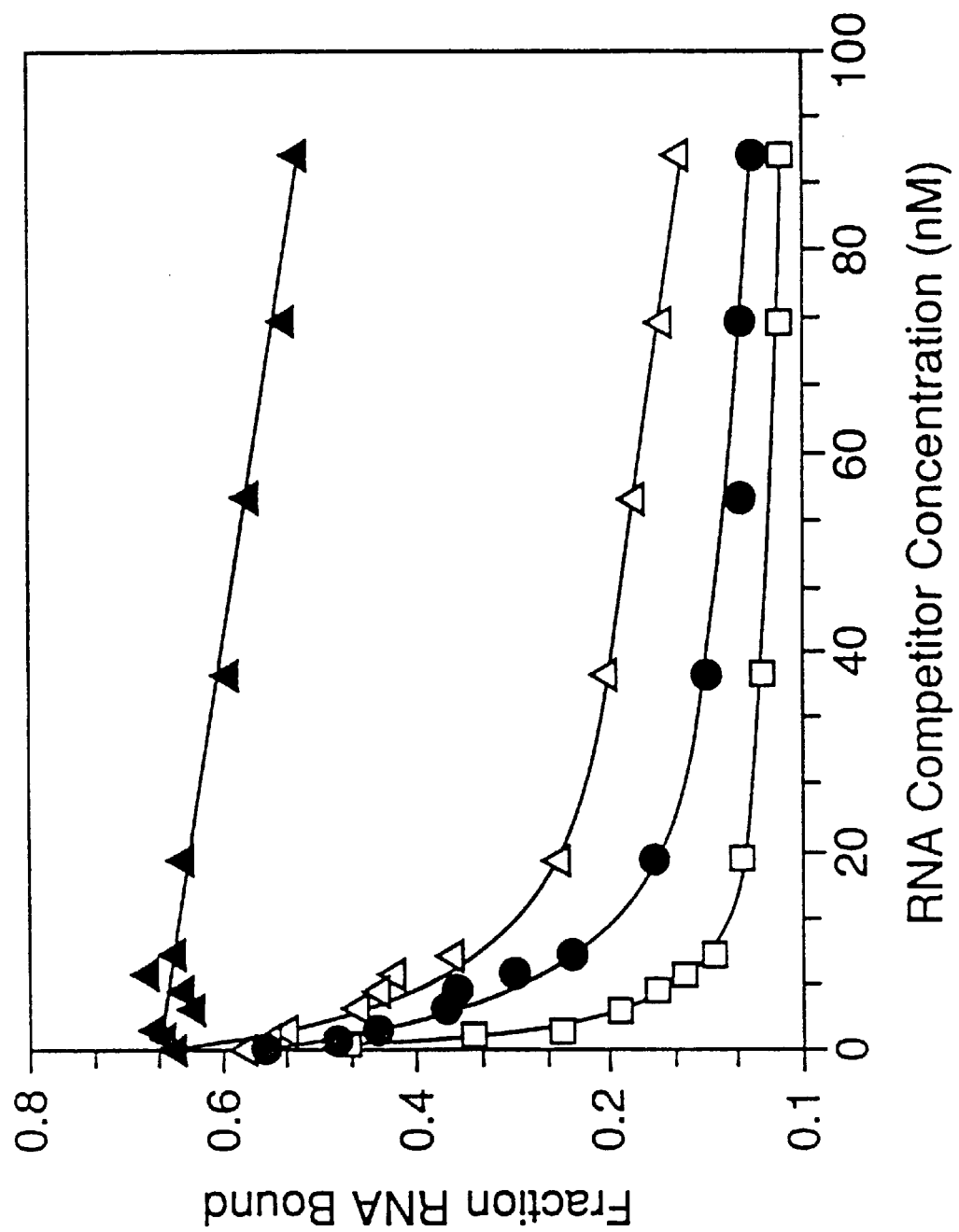
Figure 12:
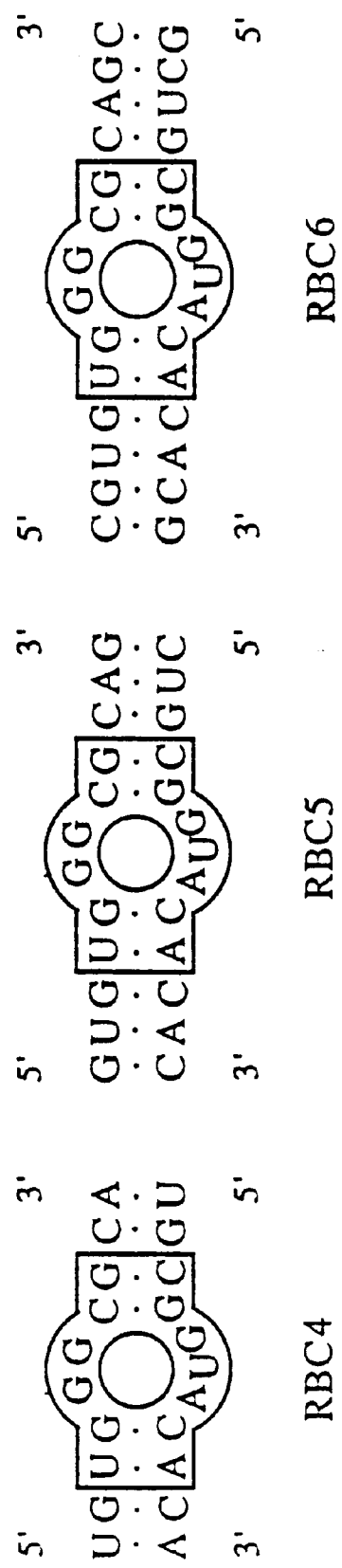
Figure 13:
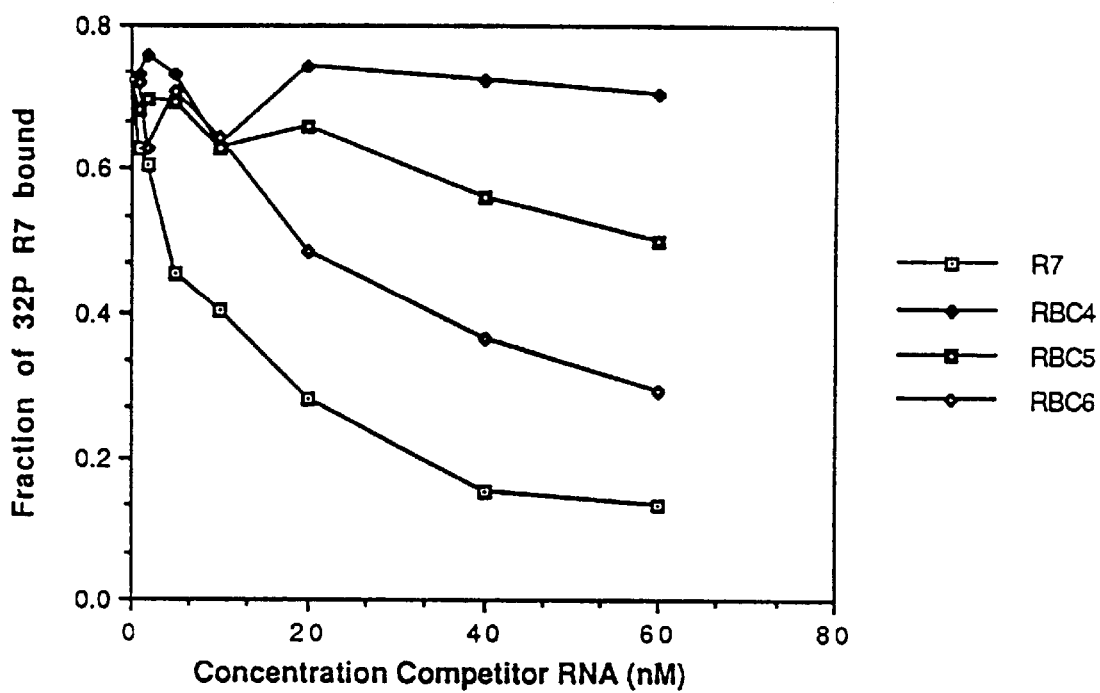
Figure 14:
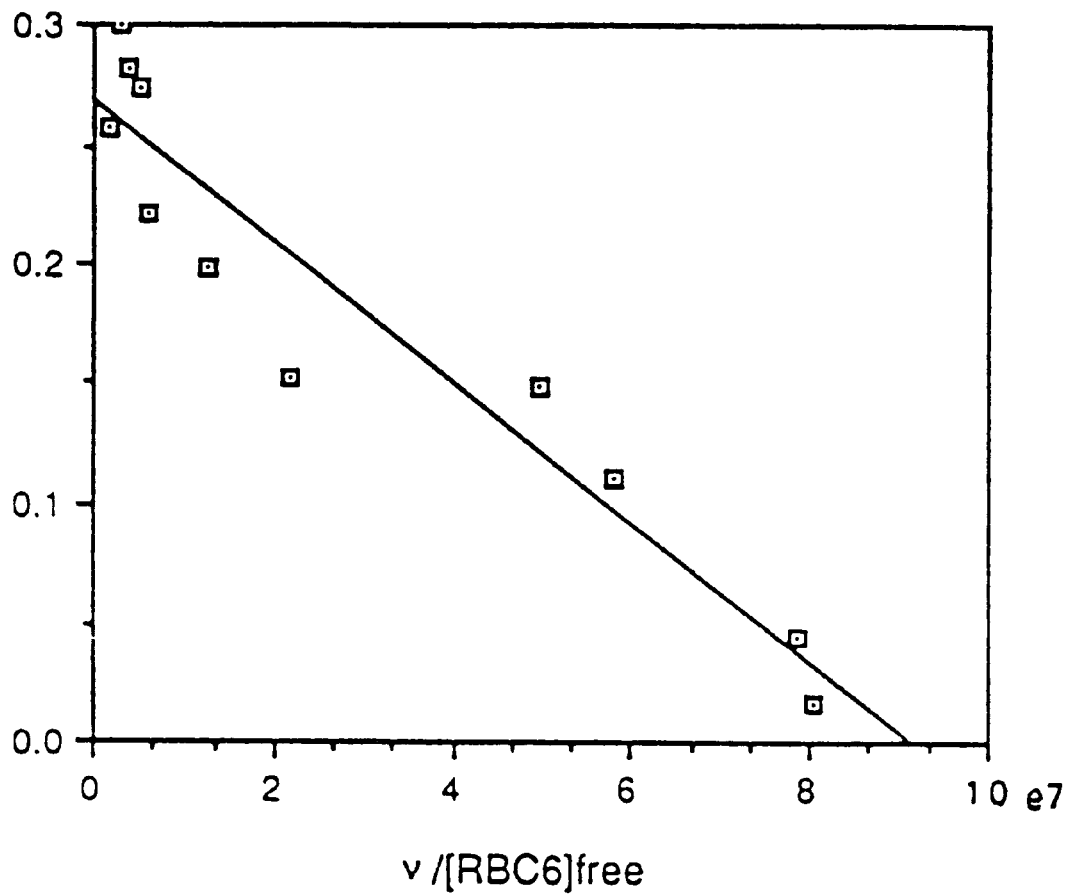
Figure 15:
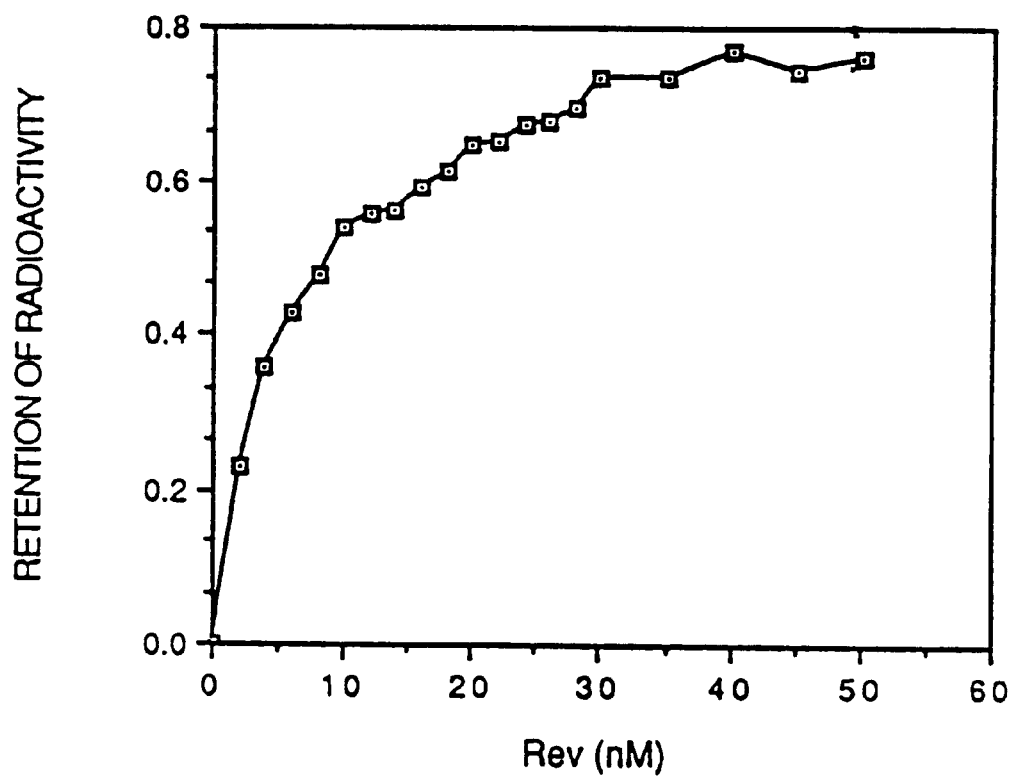
Figure 16:
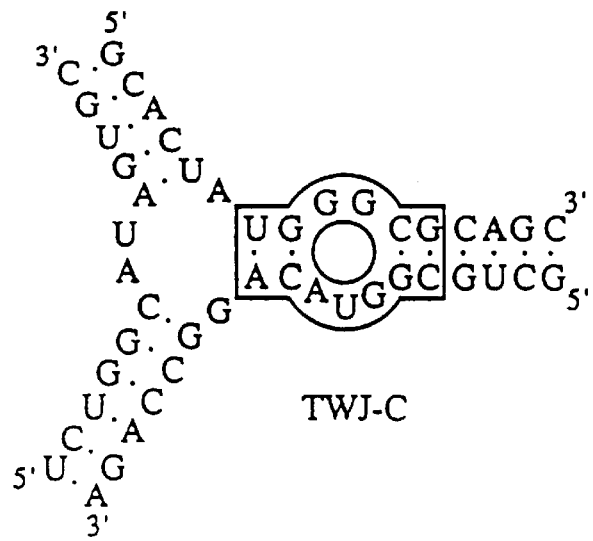
Figure 16:
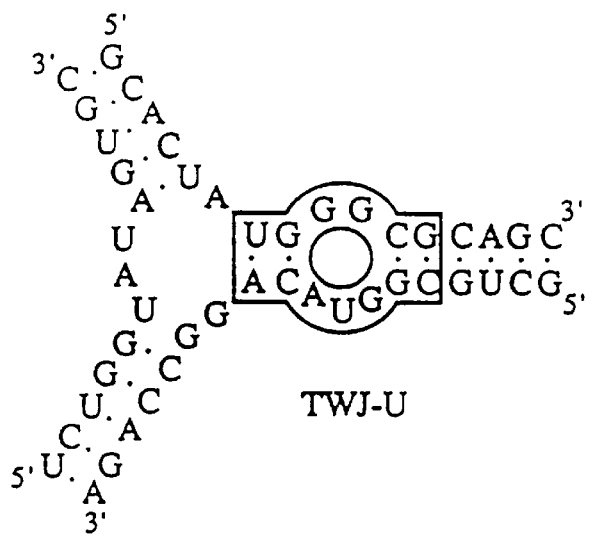
Figure 16:
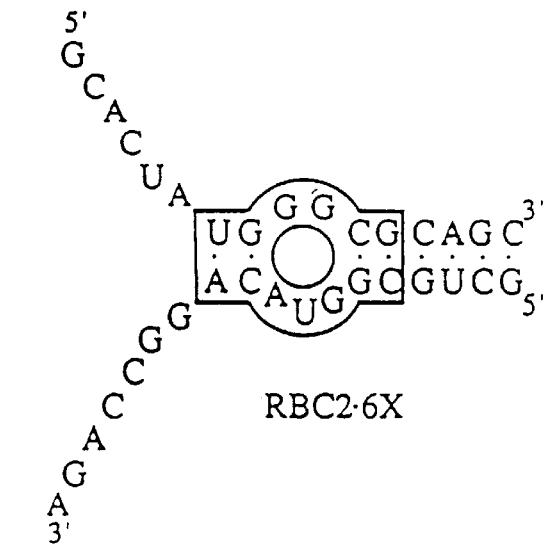
Figure 17:
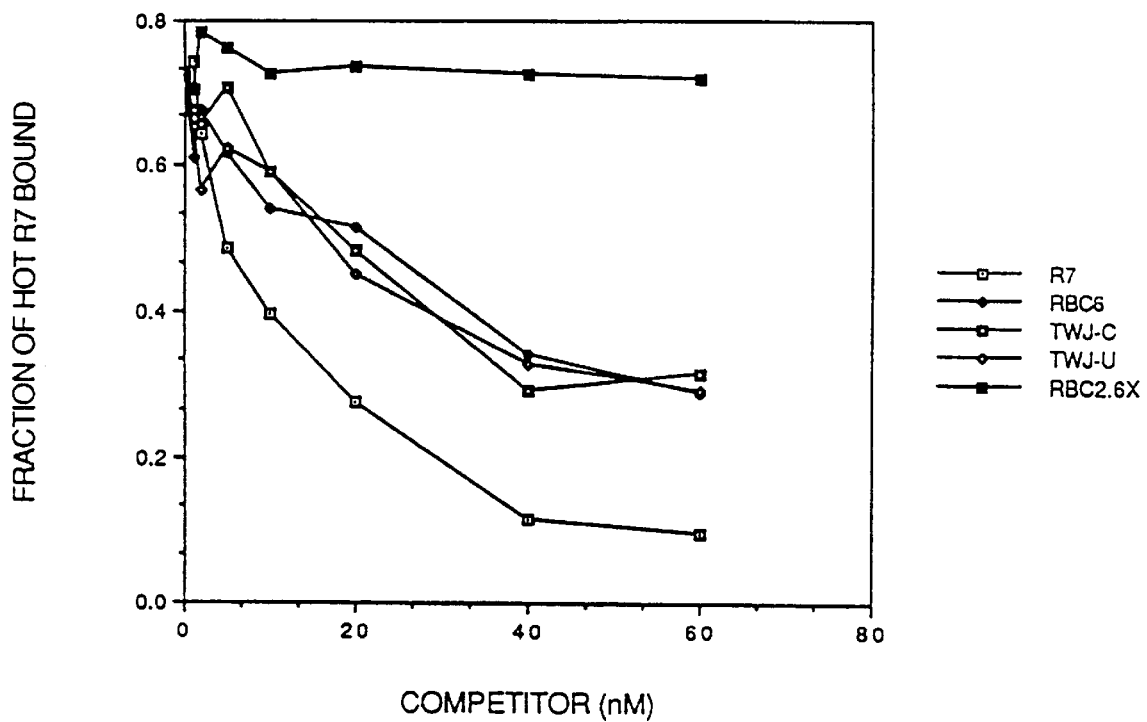

FIGS. 9a–j show the structures of short RNA transcripts carrying a high affinity rev binding site consisting of the purine-rich "bubble";

FIG. 10 is a graph of fraction RNA bound versus rev protein concentration (nM) and shows saturation binding curves for rev binding to RNA transcripts carrying a series of mutations in the purine-rich "bubble". The mutations are listed in Table 1;

FIG. 11 is a graph of fraction RNA bound versus RNA competitor concentration (nM) and shows competition binding curves for rev binding to RNA transcripts carrying a series of mutations in the purine-rich "bubble";

FIG. 12 shows the structures of chemically synthesized oligoribonucleotides which when annealed form the binding site for rev (boxed);

FIG. 13 is a graph of fraction of 32P labelled RRE RNA R7 bound versus competitor RNA concentration (nM), and shows a competition filter binding assay using the chemically synthesized oligonucleotides shown in FIG. 12 (RBC4 (filled diamonds), RBC5 (filled squares with dots), RBC6 (filled diamonds with dots)) as well as an enzymatically synthesized transcript corresponding to a 238-nucletotide long RRE sequence (R7) (empty squares with dots);

FIG. 14 shows a Scatchard plot of the binding of the chemically synthesized oligonucleotide RBC6 to rev. The structure formed by RBC6 binds approximately 4 molecules to rev protein with linear concentration dependence and a binding constant of approximately 0.3 nM;

FIG. 15 to a graph of retention of radioactivity versus rev (nM), and shows the saturation binding curve of rev protein binding to the chemically synthesized oligonucleotide RBC6;

FIG. 16 shows the structures of chemically synthesized oligoribonucleotides which when annealed form a three-way junction that stabilizes the binding site for rev (boxed);

FIG. 17 is a graph of fraction of hot ($^{32}$P labelled RRE RNA) R7 bound versus competitor (nM) and shows a competition filter binding assay using the annealed, chemically synthesized oligonucleotides shown in FIG. 16 (TWJ-C, TWJ-U, RBC2-6X); and FIG. 18a shows an electron micrograph of the filament structures formed by rev protein alone, FIG. 18b shows an electron micrograph of the filament structures formed by rev protein in the presence of 238-nucleotide long RRE RNA transcripts, and FIG. 18c shows an electron micrograph of the filament structures formed by rev protein in the presence of 2400-nucleotide long transcripts of the env mRNA, carrying an RRE sequence towards its 3' end.

DETAILED DESCRIPTION OF THE DRAWINGS

Figure 1:
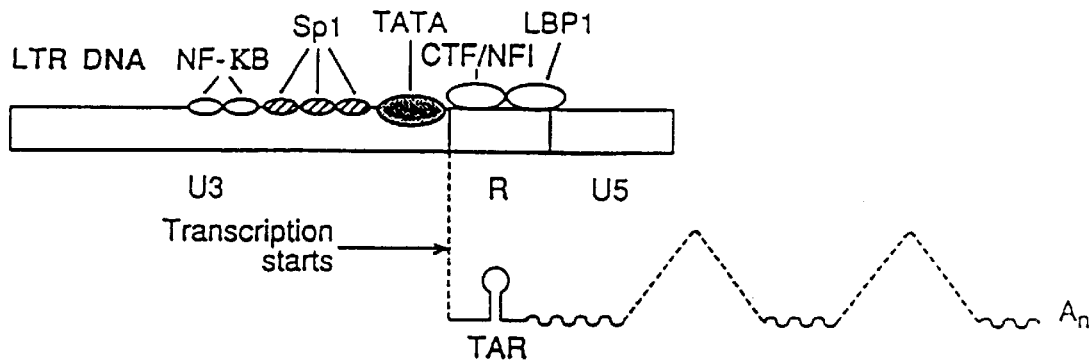
FIG. 1 illustrates the genetic elements and cellular factors controlling HIV-1 gene expressiuon.
Figure 1:
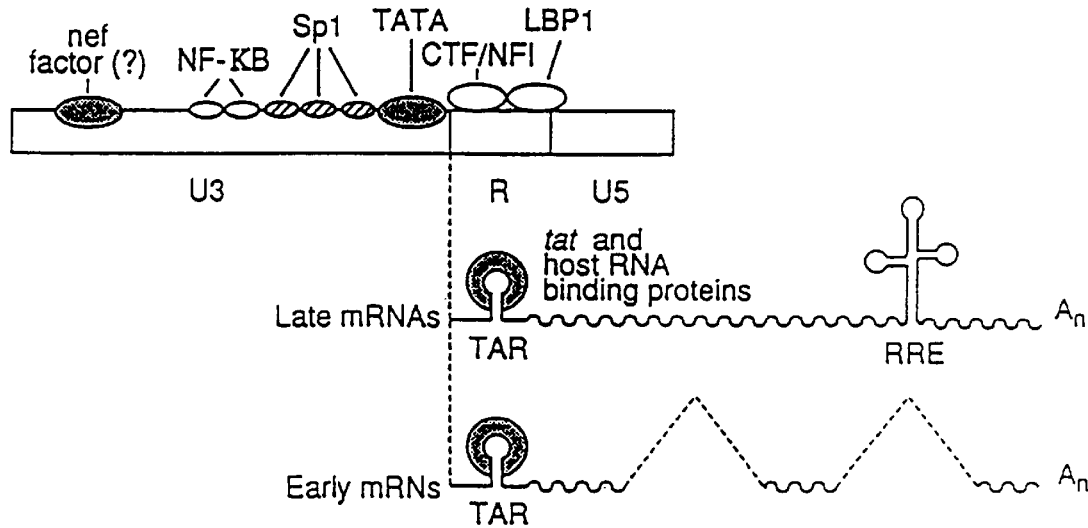
Figure 1:
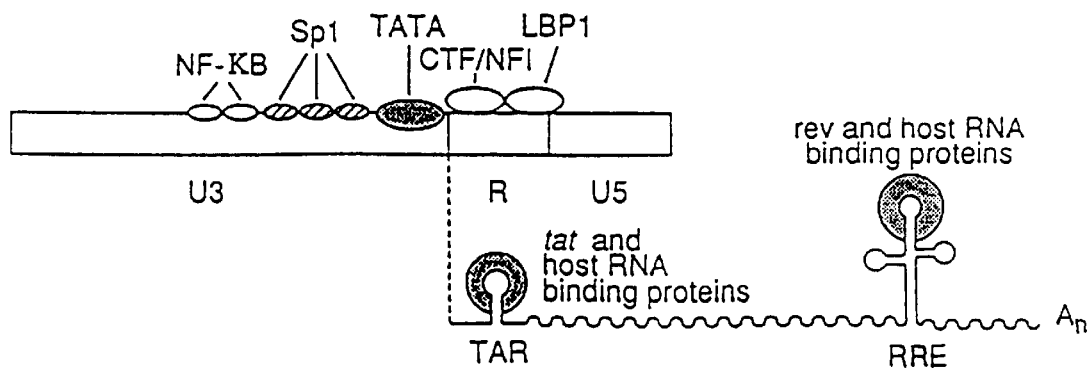

In FIG. 1 the mechanisms for control of HIV gene expression by the regulatory proteins tat and rev is shown schematically. In newly infected cells, binding of cellular transcription factors to the long terminal repeat (LTR) stimulates a basal level of transcription of the early mRNAs encoding tat, rev and nef (shown in panel 1). As tat levels rise in the cell, transcription is stimulated by the trans-activation mechanism. This leads to increased production of the early mRNAs and accumulation of partially spliced or unspliced RNA transcripts in the nucleus (panel 2). As rev levels rise in the cell, RNAs carrying the rev-response element are stabilized and exported from the nucleus. These late mRNAs act as messengers for the structural proteins encoded by the gag, pol and env genes. The full-length HIV transcript acts both as a mRNA for gap-pol and as the virion RNA (panel 3).

Figure 2:
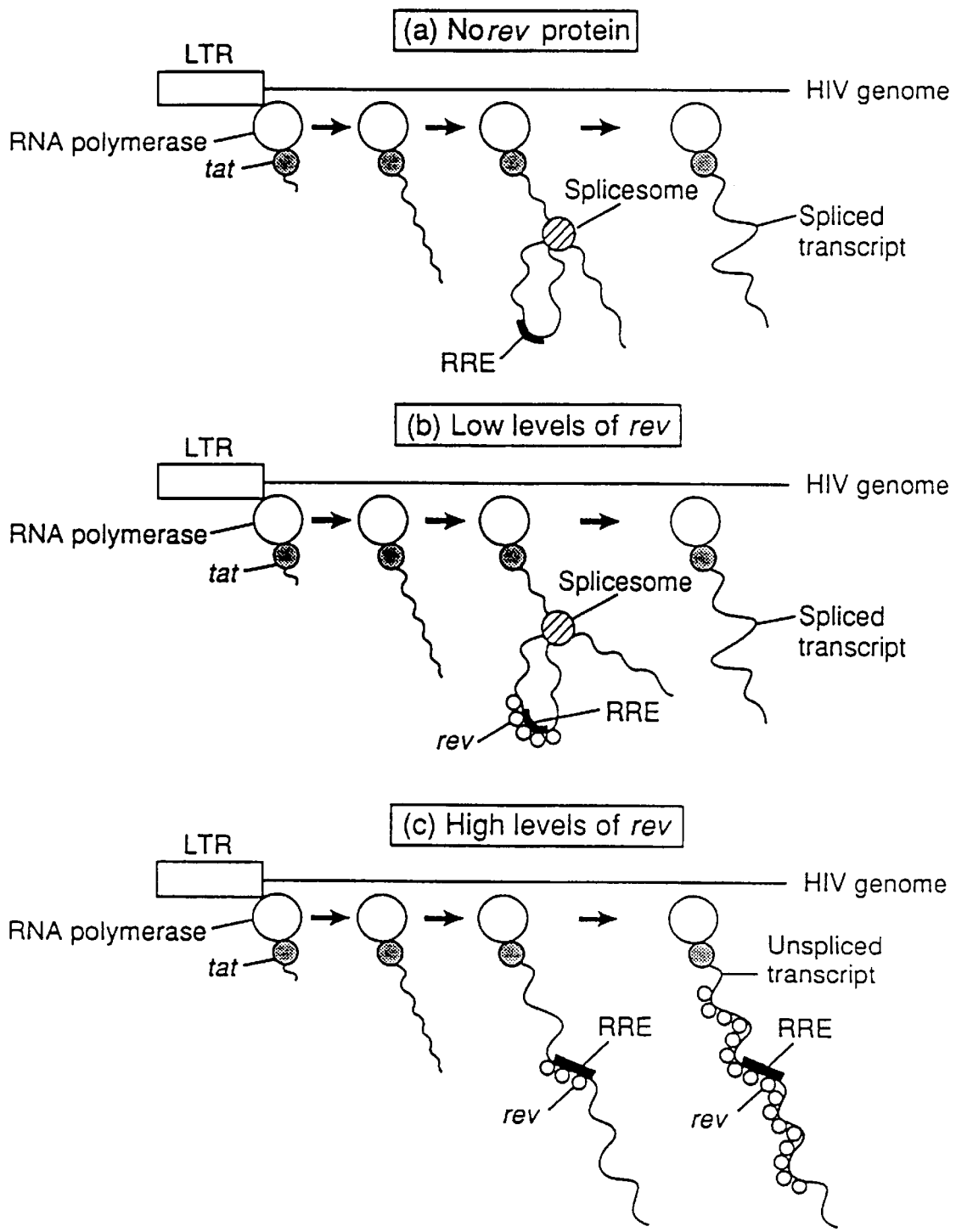
FIG. 2 shows how the RNA-binding protein rev may control HIV-1 gene expression.

FIG. 2 shows a more detailed model for control of HIV gene expression by rev. In the absence of rev, spliceosome formation and splicing is efficient (panel a). As rev levels rise in an infected cell, the protein binds to RNAs carrying the rev-responsive element, but there is insufficient protein available to effect spliceosome formation (panel b). We imagine that after a monomer or small aggregate of rev binds to the high affinity site in the RRE, additional molecules of rev could co-assemble along the length of the mRNA precursors by virtue of protein-protein and lower affinity protein-RNA interactions. Thus, at high rev concentrations RNA transcripts carying the RRE are packaged into filamentous structures (panel c). As a result of filament formation, splicing is blocked and unspliced mRNAs are exported from the nucleus. As discussed below, filament formation by this mechanism could account for the effects of rev on the processing of viral mRNAs. This mechanism is consistent with the chimical properties of rev as described below as well as the observations that the RRE is functional when placed either in an intron or in an unspliced exon (65) and is consistent with the suggestion of Change & Sharp (46) that rev disrupts spliceosome assembly. Our model also suggests that mutants of rev that block filament formation in vitro will be dominant in vivo. A number of dominant mutations of rev have already been described (67,91), and it will be of interest to determine whether these affect filament formation.

FIG. 3a shows the secondary structure for the RRE region of HIV-1$_{ARV-2}$ (residues 7786 to 8010) predicted by the RNA folding programmes of Zuker (14) SEQ ID NO: 1. Residue 1 of the RRE is the first nucleotide of the StyI site used originally to define the location of the RRE sequence (65). This corresponds to residue 12 according the numbering system of Kjems et al. (92). Our model differs from that of Malim et al. (65), because the pairing of U33, G34 and G65 with A63, C62 and U85 respectively allows formation of the purine-rich "bubble". Base pairing between residues A113 to U118 and A181 to U186 is allowed for the HIV-1$_{ARV-2}$ sequence shown above, but this feature is absent in the HIV-1$_{HXB2}$ sequence analysed by Malim et al. (65).

In panel b, the structure of the purine-rich bubble seuqnce is shown with individual bases numbered.

Figure 4:
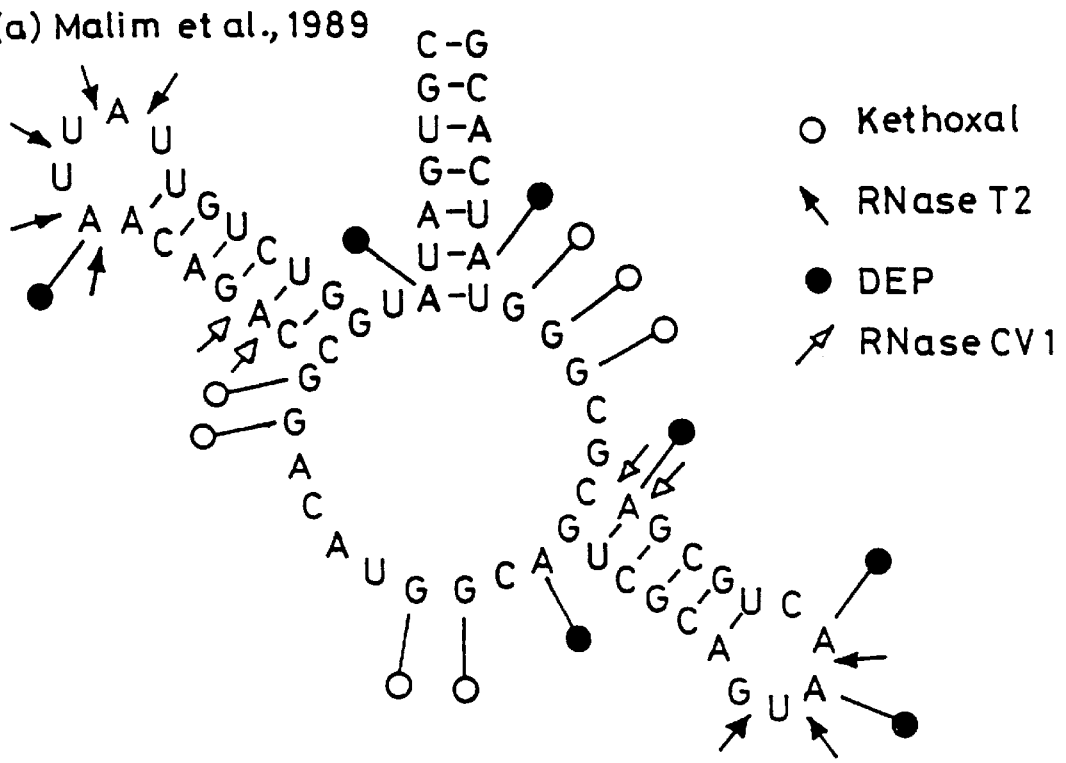
Figure 4:
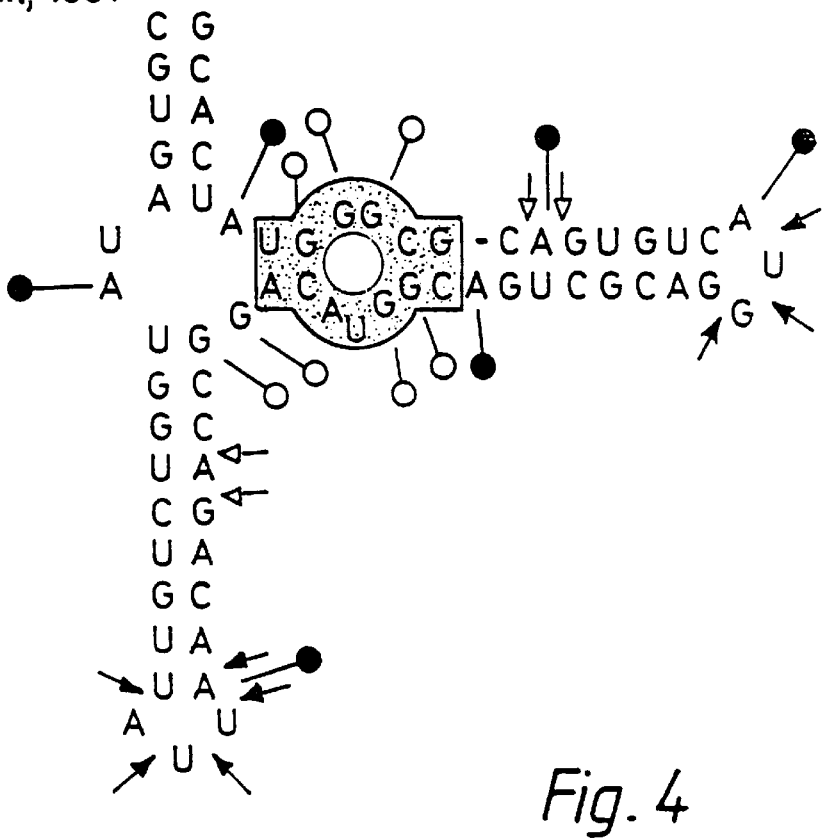

FIG. 4 compares the predicted secondary structure of the rev-response element RNA (SEQ ID NO: 2) as originally proposed by Malim et al. (65) with the corrected structure predicted using the program of Zuker. The Figure also indicates sites of enzymatic cleavage and chemical modification as determined by Kjems et al. (92): empty circles indicate kethoxal, filled circles indicate DEP, arrows with filled heads indicate RNase T2 and arrows with empty heads indicate RNase CV1. A complicated stem-loop structure for RRE RNA has been proposed by Malim et al. based on the RNA folding programs of Maizel (65,93). However, the RNA folding programs of Zuker (94) predict that a more stable structure could be formed by including the pairing of U33 and G34 with C62 and A63 on one stem and G65 with U85 respectively on an adjacent stem. As shown in the Figure, these base pairs create a purine-rich "bubble".

The new structure is more consistent with the nuclease-protection and chemical probing data reported by Kjems, et al. (92) than the model proposed by Malim et al. (65). For example, G59, G64 and G65 are strongly modified by kethoxal whereas the residues G34, G35, G36 are only weakly modified and none of these residues is susceptible to cleavage by ribonuclease T1. In the new structure, G34, G35, G36 are stacked on one side of the bulge, whereas G59, G64 and G65 appear to be more accessible. In the original model, all these residues appeared in a large open loop. Furthermore, A32 and A86, which are readily modified by diethylpyrocarbonate (92), now appear as bulged residues whereas in the original proposal these residues were base-paired.

Figure 5:
FIG. 5 illustrates rev binding to RRE fragments and shows the predicted secondary structures for RNA transcripts spanning selected regions of the rev-response element.

FIG. 5 shows the predicted secondary structures for RNA transcripts spanning selected regions of the rev-response element. These include RRE fragments 1–96, 26–92 and 26–72. Fragments corresponding to each of the transcripts were cloned into a pGEM vector and transcribed from HindIII linerise DNA using T7 RNA polymerase. The sequence GGGAGACCGGAAUUC [SEQ ID NO: 2] on the 5' end of each sequence was contributed by the vector. At the 3' end of each transcript a single A residue was contributed by the vector.

From FIG. 5 it can be seen that RRE fragments 1–96 (SEQ ID NO: 3) and 26–92 (SEQ ID NO: 4) form similar "bubble" structures in the boxed regions beginning with residue U-26. Both of these fragments bind rev with the same affinity as the full-length RRE sequence. Fragment 26–72 (SEQ ID NO: 5) includes the same sequences but does not form the same secondary structure, and in consequence, does not bind rev. Hence, not only the base sequence but also the structure represented by the "bubble" exhibited in fragments 1–96 and 26–92 is critical for rev binding activity.

Figure 6:
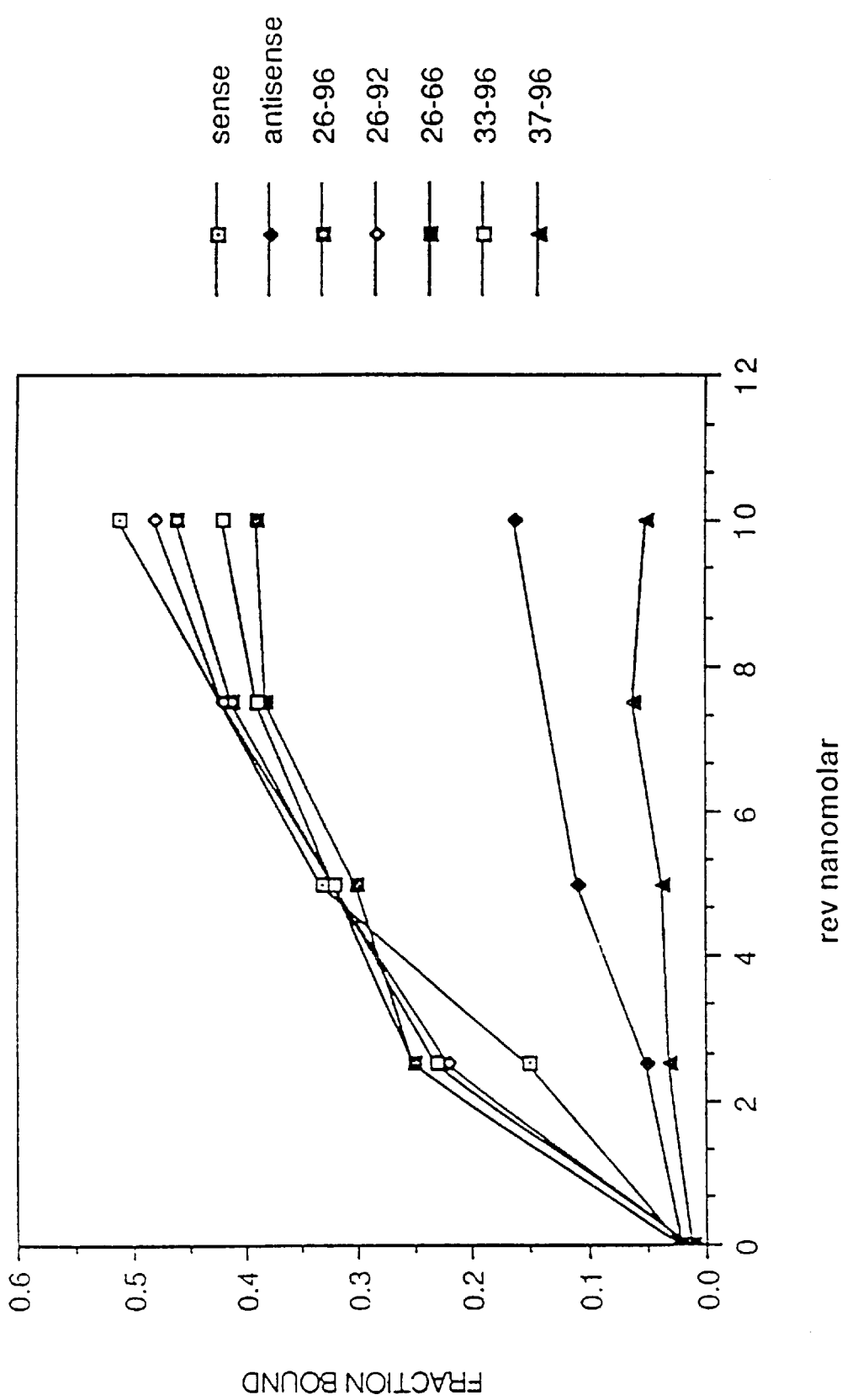
FIG. 6 is a graph of fraction bound versus rev concentration (nanomolar) and shows saturation binding curves for rev binding to RNA transcripts spanning selectd regions of the rev-response element.

FIG. 6 shows satruation binding curves for rev binding to a series of RNA transcripts spanning selected regions of the rev-response element. The "sense" sequence (indicated by empty squares with dots) is the full-length RRE sequence. Identical binding behaviour was observed using fragments including residues 26–96 (filled squares with dots), 26–92 (filled diamonds with dots), 26–66 (filled squares) and 33–96 (empty squares). However, "antisense" sequences (filled diamonds) carrying the complementary sequence to the RRE and a transcript from 37 to 96 (filled triangles) failed to bind rev efficiently. Therefore the rev binding sequence must map to between nucleotides 33 at the 5' end and 66 at the 3' end. Thus, the maximum size of the rev binding site is 34 nucleotides, and this corresponds to the predicted stem-loop structure which is necessary (and may be sufficient) for rev binding and RRE function in vivo.

These experiments strongly suggest that nucleic-acid analogues of the binding site for the regulatory protein rev are potential competitive inhibitors of regulatory protein activity in vivo. For example, a short nucleic acid seuqnece corresponding to the region of RRE RNA between residues 33 and 66 is capble of binding rev with an affinity similar to that of the complete RRE sequences. As described below, chemically synthesized sequences of even shorter length are capable of binding rev and hence inhibiting viral growth, provided that they are able to form suitable stem-loop structures.

Method

Rev protein was expressed and purified as described (33) or further purified by chromatography on Heparin-Sepharose. Rev was applied to Heparin columns in a buffer containing 220 mM NaCl/50 mM Tris-HCl pH8.0/1 mM DTT/0.1 mM EDTA 0.1% Triton X-100 and eluted in buffer containing 2 M NaCl. After gel filtration on Superose 6 (prep grade) columns equilibrated with 200 mM NaCl/50 mM Tris-HCl pH8.0/1 mM DTT/0.1 mM EDTA, the rev protein appeared homogeneous on SDS-polyacrylamide gels and free of RNA contaminants. Rev concentrations were determined by amino acid analysis of the purified protein.

DNA inserts containing RRE-related sequences were cloned between the EcoRI (5') and HindIII (3') sites of pGEM 1, either by cloning PCR products or by cloning annealed pairs of synthetic oligonucleotides. RNA transcripts for binding experiments were prepared by transcription of HindIII cut plasmids using T7 RNA polymerase and purified by gel electrophoresis. These transcripts carry a 5' extension of 15 nucleotides contributed by the vector and an extra A residue at the 3' end from the HindIII site, as described above.

For filter binding assays, each reaction mixture contained 20 pg of uniformly labelled RNA probe (approximately 500 cpm/pg RNA), 1 mg sonicated salmon sperm DNA, 0.45 mg yeast tRNA, 40 units RNasin (Promega) in 500 ml TK buffer (43 mM Tris-HCl pH8.0, 50 mM KCl). Incubation was at 4° C. for 15 minutes in the presence of 0 to 10 nM purified rev protein. In some experiments, other reagents, such as 16S rRNA were added to the binding reactions as indicated in the Figure legends. To measure binding, each reaction mixture was applied under gentle vacuum to a 0.45 um Millipore filter which had been pre-wetted with TK buffer. The filters were washed with 3×600 ml TK buffer, dried, and radioactivity counted by liquid scintillation.

Figure 7:
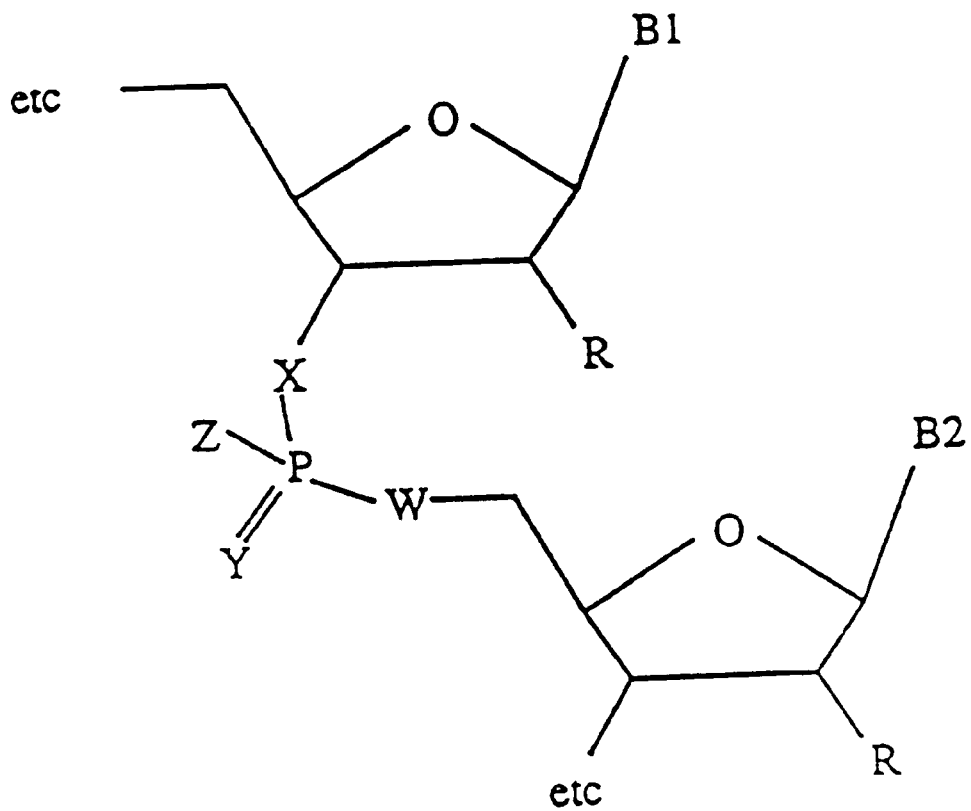
FIG. 7 shows the structures of modified oligonucleotides which might show potential anti-viral activity.

FIG. 7 shows the structures of an oligonucleotide which could be of use in the synthesis of RNA fragments with antiviral activity. Modifications to the oligonucleotide, in order to decrease its sensitivity to nuclease cleavage, or otherwise to increase its stability may include alterations to the structures of the bases B1 and B2, the sugar backbone R or the phosphate linkages W, X, Y and Z, as described above.

Figure 8:
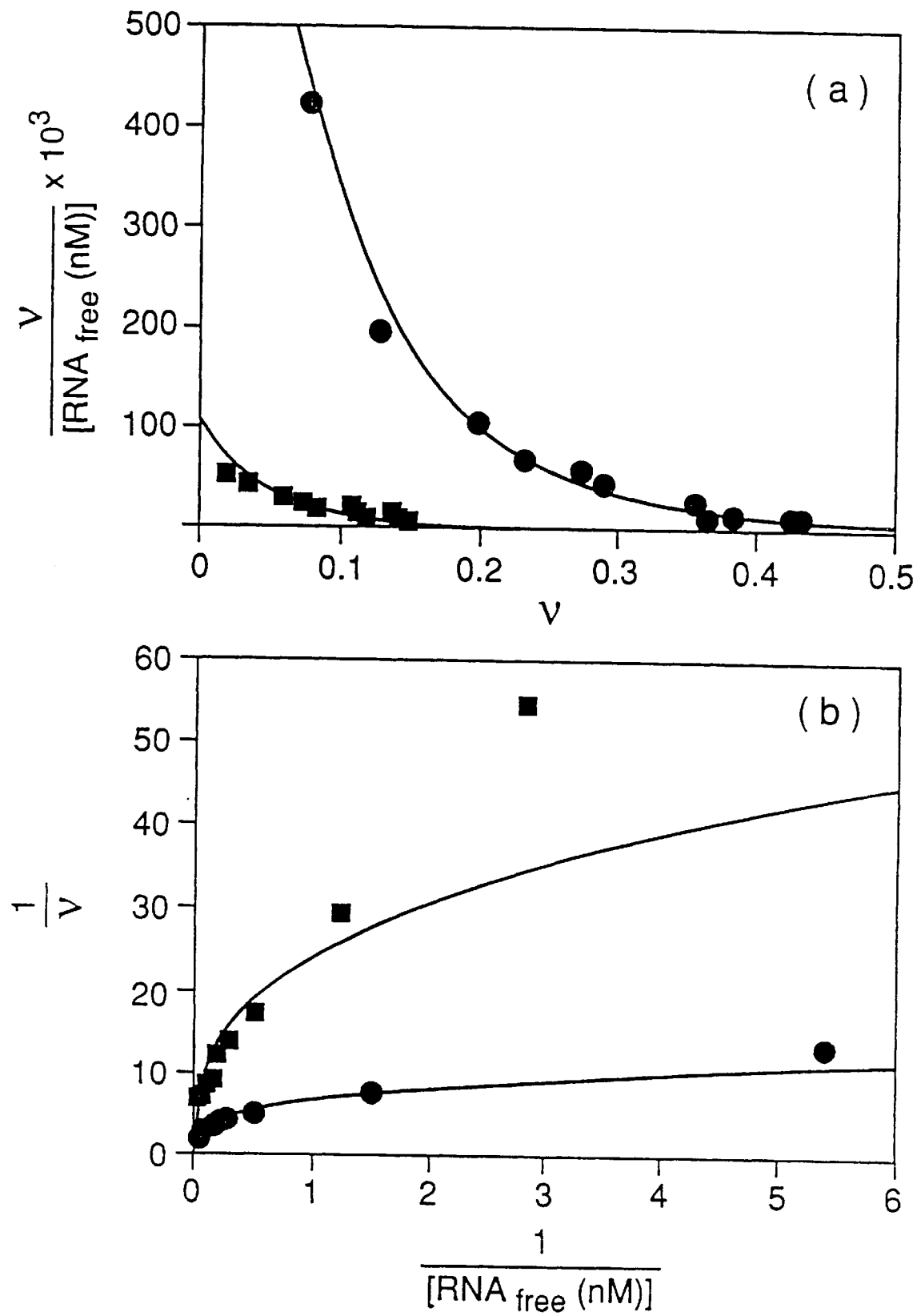
FIG. 8a shows a Scatchard analysis of rev binding to a 238 nucleotide long transcript of the rev response element.
FIG. 8b shows the same data plotted as a double-reciprocal plot.

FIG. 8 shows a Scatchard analysis of rev binding to a 225 nucleotide-long RRE RNA sequence. We have reported previously that as the concentration of rev increases, progressively larger complexes with RRE RNA are formed, whereas rev is unable to form stable complexes with anti-sense RRE and other RNA sequences (33). This experiment, which has recently been repeated by others (92), strongly suggested that rev binds initially to a high affinity site on the RRE and that subsequently additional rev molecules occupy adjacent sites. We have now shown that these additional rev molecules bind to the RRE RNA with lower affinity. As shown in FIG. 8a, the Scatchard plot for rev binding to RRE RNA is non-linear, whereas a protein which forms one-to-one complexes with RNA, such as tat, produces a linear Scatchard plot (95). In FIG. 8b the same data is plotted as a double-reciprocol plot.

We have estimated that the $K_d$ for high affinity rev binding by a linear regression analysis of the high affinity data. At 50 mM KCl (v greater than 28) there is a site to which rev binds with an apparent $K_d$ of 2±0.6 nM (50 mM KCl). At 200 mM KCl (v greater than 10) the $K_d$ for high affinity binding is 4±1.0 nM. Both these values are consistent with previous estimates of a $K_d$ of between 1.0 and 3.0 nM obtained from saturation binding experiments (33,34). However, it should be noted that estimates of $K_d$ by any simple binding experiment that uses labelled RNA as a probe will include the contributions of both the high affinity site and the adjacent lower affinity sites (96).

The stoichiometry of rev binding to RRE RNA is highly dependent on ionic strength. At 50 mM KCl between six and eight rev monomers bind to the RRE RNA, whereas the stoichiometry of binding is approximately 2:1 at 200 mM KCl (FIG. 1b). In agreement with previous reports (11), we have found that rev elutes from gel filtration columns equilibrated with 200 mM NaCl with an apparent mass of 60 kDa (data not shown). These results suggest that rev exists in solution as a small oligomer, most likely a tetramer (11,12), that is able to bind to RNA.

Method

Binding reactions were performed in buffers containing 50 mM Tris-HCl pH8.0, 1 ug sonicated salmon sperm DNA, 0.45 ug of yeast tRNA and 20 units of RNAsin (Promega) and either 200 mM KCl (filled circles) or 50 mM KCl (filled squares). Reactions at 200 mM KCl contained 9 to 10 nM rev and between 1 to 90 nM RRE RNA. Reactions at 50 mM NaCl contained 30 to 34 nM rev and between 1 to 90 nM RRE RNA. In FIG. 8a the data is plotted as the stoichiometry, v (the ratio of the concentration of bound RNA to rev protein; abscissa) versus the ratio of v to the free RNA concentration (ordinate). In FIG. 8b, the data is plotted as the reciprocal of the stoichiometry versus the reciprocal of the free RNA concentration.

Figure 9:
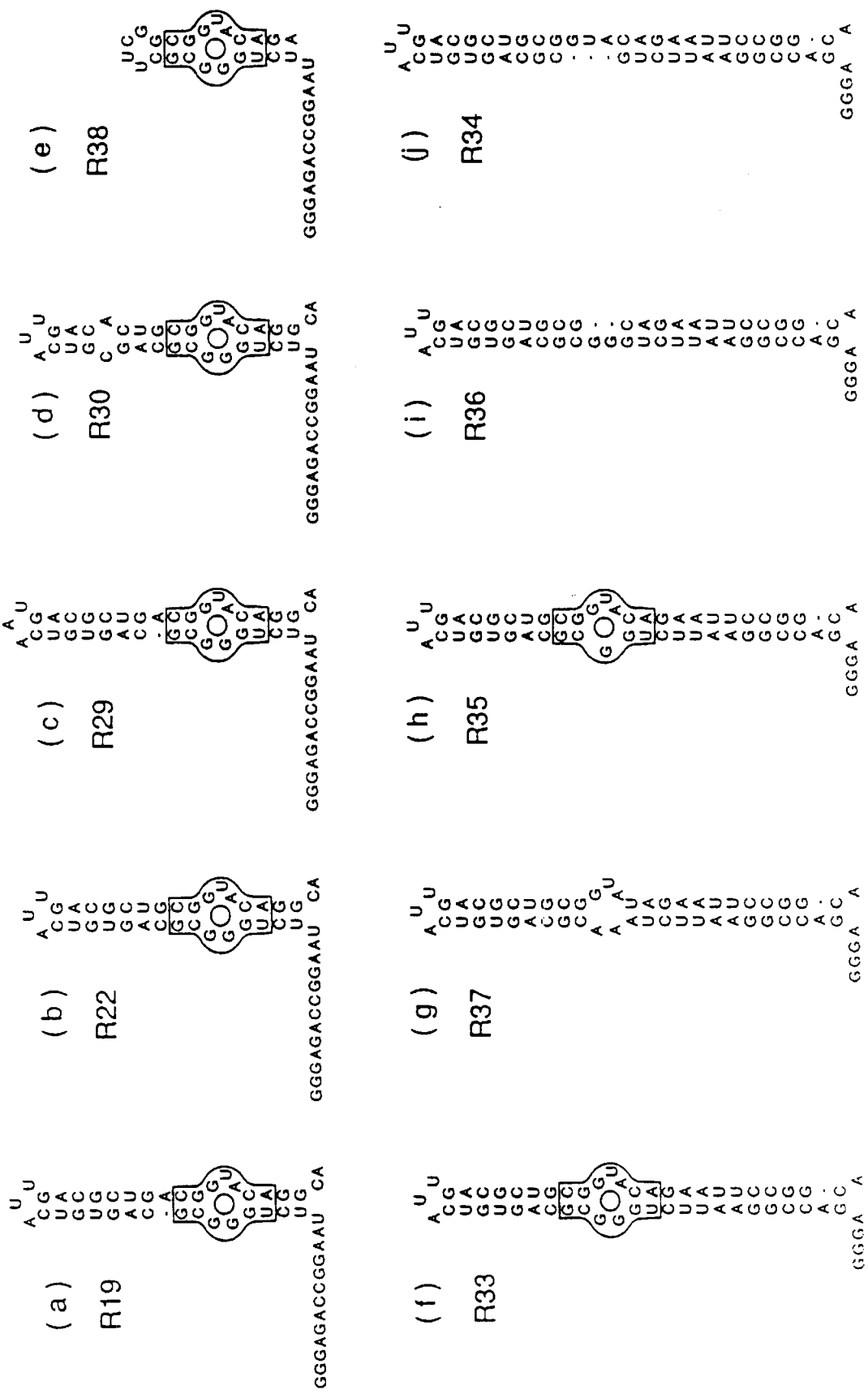

FIG. 9 shows representative short RNA stem-loop structures assayed for rev-binding. The sequences shown represent the full transcripts including residues derived from vector sequences. The optimal structures predicted by the method of Zuker (94) are shown, with the purine-rich "bubble" boxed. (a) Transcript R19 (SEQ ID NO: 6) contains RRE sequences 33 to 66. (b) R22 (SEQ ID NO: 7), residue A56 is deleted from R20. (c) R29 (SEQ ID NO: 8), residues are altered in the apex of the loop to give the anti-sense sequence. (d) R30 (SEQ ID NO: 9) base pairing in the upper stem structure is altered to give the anti-sense sequence. (e) R38 (SEQ ID NO: 10), the stem-loop structure C39 to A56 is replaced by the stable loop sequence CUUCGG (15). (f) R33 (SEQ ID NO: 11), the stem-loop formed by residues 33 to 63, with residue A56 deleted, was inserted on top of a stem containing 9 base pairs. (g) R37 (SEQ ID NO: 12), the purine-rich bubble is replaced by an altreed sequence carrying bulged A residues on the 5' side. (h) R35 (SEQ ID NO: 13), the purine-rich bubble is replaced by an altered sequence carrying a single bulged G residue on the 5' side. (i) R36 (SEQ ID NO: 14), the bulged residues G59-A61 are deleted. (j) R34 (SEQ ID NO: 15), the bulged residues G35, G36 are deleted.

As described above the high affinity rev binding site is located between residues A26 and A96. The shortest T7 transcript that is able to bind rev with a $K_d$ of 1–3 nM includes RRE sequences beginning at U33 and ending at C66 (R19.) This sequence is predicted to fold into the stable stem-loop containing the purine-rich "bubble" shown in FIG. 3. The structure is stabilized by a four-base pair stem below the "bubble" which contains CU residues derived from the T7 leader sequence.

Only the boxed sequences in the "bubble" region are required for rev binding. Deletion of the bulged A, at residue 56 (R22) or replalcement of the entire upper stem sequence with the stable RNA hairpin loop sequence CUUCGG (R38) produced transcripte which bound rev with $K_d$=1–3 nM.

Similarly, replacement of the upper stem and loop by antisense sequences (R20, R30) resulted in transcripts with normal rev binding activity.

Normal rev binding was also observed when the purine-rich "bubble" was inserted into an elongated RNA stem-loop structure (R33). The bulged residues on both sides of the purine-rich "bubble" are required for specific rev binding. Deletion of G59, U60 and A61 created a structure with a G, G bulge on one side of the helix (R36) and resulted on loss of rev binding. Deletion of G35 and G36 from the other side of the helix (R34) or replacement of these residues with bulged A residues (R37) also abolished specific rev binding. Deletion of G35 alone only reduced rev binding slightly (R35).

FIG. 10 shows saturation binding curves for rev binding to RNA transcripts carrying a series of mutations in the purine-rich "bubble". The truncated RRE RNA transcripts containing the rev binding site can bind to rev with a dissociation constant similar to that of full-length RRE (i.e. $K_d$=1–3 nM). Because the R33 RNA is in a very stable predicted (conformation delta G•=−29.6 kcal/mol), we were able to introduce deletions and substitutions within the purine-rich "bubble" region of R33 RHA without disrupting its overall structure (Table 1).

The results are represented as follows:

| | |
|---|---|
| R7 | empty square with dot |
| R33 | filled diamond |
| R34 | filled square with dot |
| R44 | filled diamond with dot |
| R49 | filled square |
| R50 | empty square |
| R52 | filled triangle |
| R53 | filled triangle with dot |
| R54 | filled square |
| R55 | cross |
| R57 | empty square with cross |

Nucleotide substitutions (Table 1) are tolerated at the U60 residue (R52), and a G36 (R50) but deletions or substitutions affecting the other bulged residues resulted in complete loss of specific rev binding. For example, replacement of G35 with A (R47) or A61 with G (R53) abolished rev binding.

The four base pairs immediately adjacent to the bulged residues in the purine-rich "bubble" are also important for rev binding (Table 1). Replacement of C37:G58 with a G:C base pair (R41) or replacement of G34:C62 with a C:G base pair (R40) abolished specific rev binding. Alterations to the other base pairs in the "bubble" region also reduced rev binding significantly (Table 1). The only neutral mutation that we discovered was in R57, in which the base pair G38:C57 is replaced by an A:U base pair.

FIG. 11 shows competition binding curves for rev binding to RNA transcripts carrying a series of mutations in the purine-rich "bubble". unlabelled RRE RNA was an effective competitor and reduced rev binding to the labelled RRE RNA by 50% of the initial value with a $D_{1/2}$=2 nM. The short R33 transcript was also an effective competitor and reduced rev binding with $D_{1/2}$=8 nM. The mutations in the "bubble" either reduce or abolish specific rev binding. For example, R34, which carries a deletion of the bulged G residues G35 and G36, does not bind rev with measurable affinity and did not compete efficiently for rev binding against the RRE ($D_{1/2}$ greater than 250 nM). R35 which has a bulge containing a single residue, and is typical of a mutation with reduced rev affinity had a $K_d$ of 4 nM and showed intermediate competition behaviour ($D_{1/2}$=16 nM).

Method

Filter binding reactions contained 17 nM rev, 0.5 pM labelled RRE RNA and between 0–100 nM unlabelled competitor RNA. Empty squares, RRE RNA competitor; filled circles, R33 RNA competitor; filled triangles, R34 RNA competitor; empty triangles, R35 RNA competitor.

The binding of chemically synthesized RNA by rev protein (FIGS. 12–15).

FIG. 12 shows the structures of small RNA duplexes containing a purine-rich bubble. Boxed residues are those which have been shown to be essential for specific recognition by rev protein: RBC4 (RBC is an abbreviation for Rev Binding Core) has 4 base pairs in the stem on each side of the bubble (SEQ ID NO: 16 and SEQ ID NO: 17). Similarly RBC5 has 5 base pairs (SEQ ID NO: 18 and SEQ ID NO: 19) and RBC6 has six base pairs on each side (SEQ ID NO: 20 and SEQ ID NO: 21). The oligoribonucleotides were synthesised chemically essentially as described (1) and purified by reversed-phase HPLC. When annealed pairwise the oligonucleotides can form duplexes containing the recognition site for tat protein.

FIG. 13 shows the results of a competition filter binding assay to compare the binding to rev of the chemically synthesized duplexes with that of a 238-base RRE transcripts (R7). In these experiments, uniformly $^{32}$P-labelled R7 (1.5 nM) was competed against 0–60 nM unlabelled competitor RNA in the presence of 24 nM rev protein. The results show that RBC6, which has 6-bp stems, competed about half as well as R7, while RBC5 and RBC4 had less and no competitive binding abilities respectively. These results demonstrate that small duplexes consisting of chemically synthesized oligonucleotides can bind to rev protein and act as inhibitors of rev.

FIG. 14 shows a Scatchard analysis of the binding of RBC6 to rev. Binding experiments were carried out using labelled RBC6 duplex formed frm the 5'—$^{32}$P-labelled 14-mer oligoribonucleotide annealed to the 15 mer (0.6 nM) and 0–150 nM unlabelled RBC6 in the presence of 24 nM rev protein. The results show that the stoichiometry of protein: RNA is approximately 4:1 and that the dissociation constant ($K_d$) is approximately 3 nM, a value very similar to that for full length RRE interaction with rev. Also the linearity of the graph shows that there are no lower affinity binding sites for rev protein on RBC6 in contrast to full length RRE which shows a non-linear Scatchard plot. FIG. 15 shows the result of saturation binding experiments using 1.5 nM $^{32}$P labelled RBC6 and 0–50 nM rev. From these data, a Scatchard plot gave a straight line with a $K_d$ value of 3.8 nM.

Method a) Chemical Synthesis of Oligoribonucleotides

This was carried out on an Applied Biosystems 380B Synthesizer essentially as described (100) using protected ribonucleoside 3'—phosphoramidites purchased from MilliGen. After deprotection, the oligoribonucleotides were purified by reversed-phase HPLC using a uBONDAPAK C18 column (7.8 mm×300 mm) with a linear gradient of acetonitrile in 0.1M triethylammonium acetate buffer (pH7.0). The purity of each oligonucleotide was analysed by anion-exchange HPLC using a HICHROM P10SAX column (10 mmID×250 mmL) with a linear gradient of potassium phosphate (pH6.3) in formamide-water (3:2, v/v). After desalting using a Sephadex NAP-10 column (Pharmacia), two appropriate oligonucleotides were annealed by mixing (typically 500 pmol each in 50 ul of water) by heating at 90° C. for 2 min and by cooling gradually to room temperature.

b) Preparation of Labelled and Unlabelled R7 transcript

The mixtures for transcription reaction (500 ul for $^{32}$P-labelled and 100 ul for unlabelled) included 0.1 mg/ml template HindIII cut plasmid DNA, 32 mM Tris-HCl (pH7.4), 20 mM NaCl, 13 mM MgCl$_2$, 8 mM DTT, 2.4 mM each of ATP, GTP, CTP and UTP, 800 units/ml RNasin (Promega) and 1–15 units/ul T7 RNA polymerase. For radiolabelling, 100 uCi of (alpha-$^{32}$P) UTP was added. The reaction was allowed to proceed for 2 hr at 37° C. and stopped by addition of EDTA to 30 mM. After phenol extraction, the solution was concentrated by butanol extraction, and the 238-base transcript was purified by 6% polyacrylamide gel electrophoresis followed by elution with 0.5M ammonium acetate, 1 mM EDTA (pH7.4) and 0.5% sodium dodecylsulfate, butanol extraction and ethanol precipitation.

c) Competition Assay

The mixtures for competition binding (0.5 ml) included 1.5 nM $^{32}$P-labelled R7 (ca. 20,000 cpm), 24 nM rev protein, 1.5 ug/ml calf thymus DNA, 0.67 ug/ml yeast rRNA, varying concentrations (0–60 nM) of unlabelled competitor RNA and 80 units/ml RNasin in TK buffer (50 mM Tris-HCl (pH7.9) and 20 mM KCl). Binding was allowed to take place for more than 15 min on ice, and each mixture was passed through a Millipore GS filter (a 2.5 cm disk with a pore size of 0.22 um) prewashed twice with 0.6 ml of ice-cold TK buffer. The filter was washed with 0.6 ml of cold TK buffer and dried. The radioactivity retained on the filter was counted by liquid scintillation, and the results were plotted on a graph (FIG. 13).

d) Preparation of Labelled RBC6

The mixture of 5'-labelling (50 ul) included 500 pmol of the 14 mer, 50 mM Tris-HCl (pH7.6), 10 mM MgClhd 2, 5 mM DTT, 50 ug/ul BSA, 20 uM ATP, 50 uCi of (gamma-$^{32}$P)ATP, 80 units/ml RNasin and 10 units of T4 polynucleotide kinase (BioLabs). The reaction was allowed to proceed for 1 hr at 37° C. After heating in boiling water for 2 min, the labelled 14-mer was purified by 20% polyacrylamide gel electrophoresis, eluted with water and desalted using a Sephadex NAP-10 column. Annealing to the 15-mer was carried out as described above.

e) Binding of RBC6 to Rev Protein

The mixtures for binding (0.5 ml) included 0.6 nM $^{32}$P-labelled RBC6 (ca. 20,000 cpm), 24 nM rev protein, varying concentrations (0–150 nM) of unlabelled RBC6 and 80 units/ml RNasin in TK buffer. The filter binding assays were carried out as described above, and a Scatchard plot (FIG. 14) was obtained from the results. The x intercept shows the stoichiometry of RNA to rev protein, and the $K_d$ value is derived from the slope.

f) Saturation Binding of Rev Protein to RBC6

The mixtures for binding (0.5 ml) included 1.5 nM $^{32}$P-labelled RBC6 (ca. 20,000 cpm), varying concentrations (0–50 nM) of rev protein and 80 units/ml RNasin in TK buffer. The filter binding assays were carried out as described above, and the results were plotted on a graph (FIG. 15).

FIG. 16 shows the structures of synthetic oligoribonucleotides which can anneal to form a "bubble" structure stabilized by a "three-way" junction similar to that found in the rev-response element. TWJ-U (SEQ ID NO: 22, SEQ ID NO: 23 and SEQ ID NO: 25) carries an authentic HIV-1$_{ARV2}$ sequence with a G:U base pair formed between G25 and U85. In TWJ-C (SEQ ID NO: 22, SEQ ID NO: 23 and SEQ ID NO: 24) U85 has been replaced by a C to form a slightly more stable structure. In RBC2-6X only two oligonucleotides are annealed. Although this pair of oligonucleotides contains all the sequences from the "bubble" region, this structure is not sufficiently stable to form an effective rev binding site.

Figure 3:
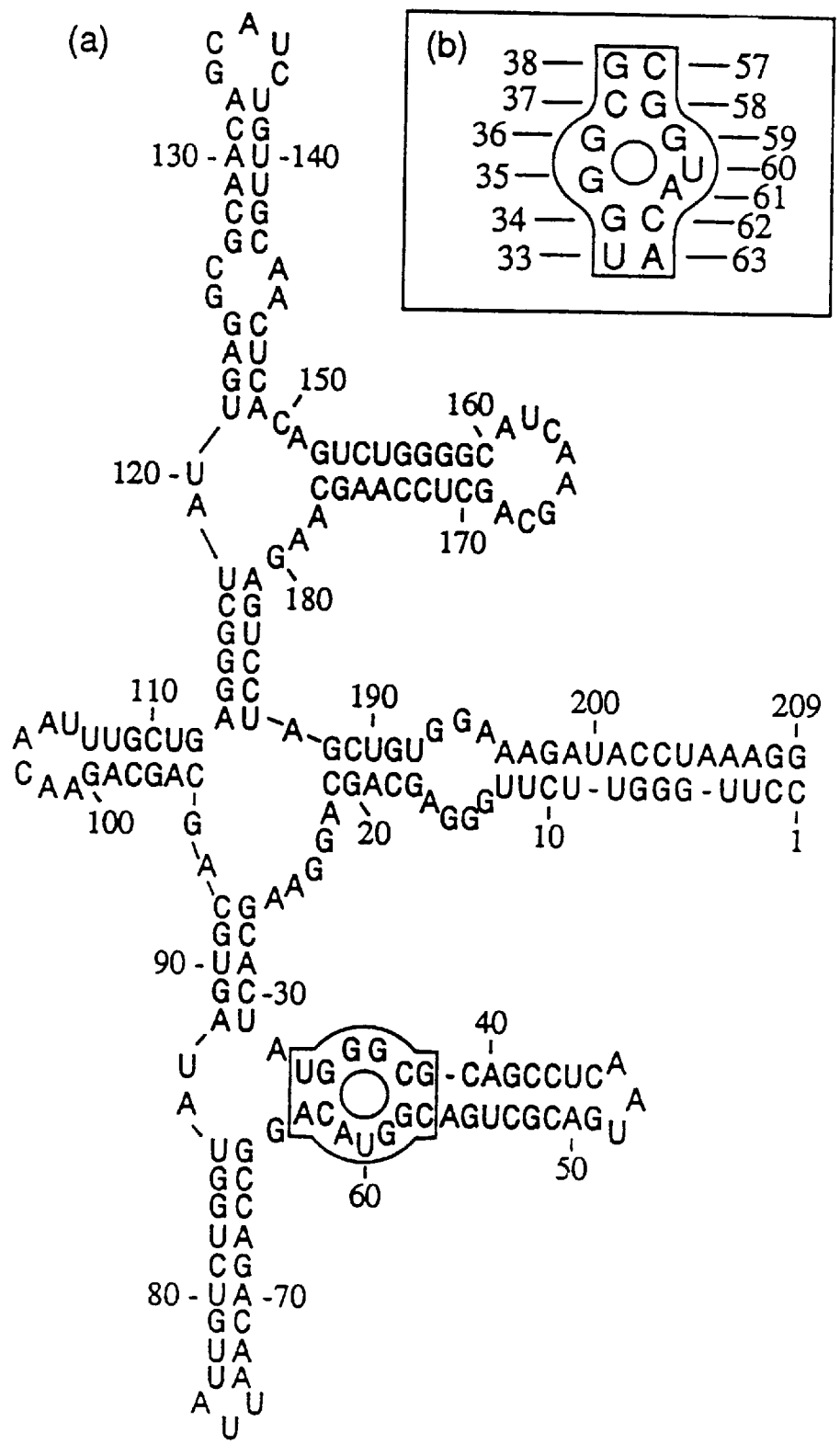
FIG. 3 shows the structure of the rev-response element RNA folded according to the program of Zuker (SEQ ID NO: 1)

FIG. 17 shows competition binding curves for rev binding to the synthetic ribonucleotides forming the "three-way" junction and "bubble" structures. Results for R7 are indicated by empty squares with dots. The TWJ-C (SEQ ID NO: 22, SEQ ID NO: 23 and SEQ ID NO: 24) (filled squares with dots) and TWJ-U (SEQ ID NO: 22, SEQ ID NO: 23 and SEQ ID NO: 25) (filled diamonds with dots) junctions both compete for rev binding with the same affinity as the "bubble" structure created by the RBC6 (filled diamonds) binding site. By contrast, RBC2, 6X (filled squares), which contains only two oligonucleotides is unable to compete effectively. Thus in order to act as a rev binding site the sequences comprising "bubble" structure must be stabilized by flanking secondary using either double-helical structural elements as in RBC6 or a three-way junction as in TWJ-C and TWJ-U. In addition to demonstrating that synthetic three-way sequences can act as a binding site for rev, these data also provide further support for the model for the secondary structure of the rev-responsive element as shown in FIGS. 3 and 4b. In the predicted structure, the "bubble" sequence is also stabilized by a three-way junction.

Figure 18:

FIG. 18 shows electron micrographs of filaments formed by rev protein alone (panel a) or in complexes with the 22 nucleotide long RRE RNA transcript (panel b) or in complexes with a 2.4 kb transcript corresponding to env mRNA. Samples were negatively stained with uranyl acetate (120, 000 X).

At concentrations above 100 ug/ml rev polymerizes in low salt buffers (50 mM NaCl) and forms a gel (33). Electron micrographs show that these gels contain large filaments about 14 nm wide and up to 1,500 nm long. Filament formation is temperature dependent, and the longest filaments are grown by slowly increasing the temperature from 4° C. to 25° C. over a period of several hours, suggesting that filament formation is an entropically driven process that is dependent upon hydrophobic interactions between rev molecules. The structure of the rev-containing filaments is fairly regular, with units which are spaced at approximately 4 nm. There is a band of negative stain running down the middle of the filaments, suggesting that they are hollow tubes.

When an excess of rev is mixed with the 238-long RRE 7 transcript, short rod-like ribonucleoprotein complexes with a preferred filament length of 60 nm are formed. Filaments as long as 500 to 700 nm have been detected when a 2.4 kb transcript of the env gene is used as a template. The ratios of these two filament lengths suggests the RNA molecules are coated throughout their entire lengths. The samples examined by electron microscopy were also analyzed by sucrose gradient centrifugation and, in the case of the 238 RRE RNA fragment, by non-denaturing gel electrophoresis (33). All the RNA transcripts were bound by rev and produced high molecular weight complexes that could be easily distinguished from free RNA and were protected from digestion by micrococcal nuclease (data not shown).

Method

Protein filaments were grown from solutions containing 20 to 100 ug/ml rev protein in 20 mM Tris-HCl pH7.4, 50 mM NaCl, 1.0 mM DTT by slow warming from 4° C. to 25° C. for a period of several hours. Protein filaments are not formed with rev exposed to Triton X-100. Complexes between rev protein and RNA transcripts carrying an RRE sequence at the 5' end were formed using 0.01 to 0.1 ug/ml RNA, and 22 to 110 ug/ml rev protein in 20 mM Tris-HCl pH7.4, 50 mM NaCl, 0.1 mM EDTA, 1.0 mM DTT, 20 units/ml RNasin at 30° C. for 1 hour. Complex formation was monitored by gel mobility shift assays (7), surcrose gradient centrifugation and electron microscopy. Filaments were negatively stained with uranyl acetate and photographed at a magnification of about 50,000 X.

Discussion

The complex binding behaviour of rev has led to some confusion as to whether rev recognises a secondary structure or a specific sequence feature in the RRE RNA (92,73,97). The work reported here demonstrates that the RRE contains a purine-rich "bubble" which acts as the high affinity rev-binding site. However, because of its ability to polymerize, rev is also able to bind RNA sequences adjacent to the high affinity site. The binding of rev to those lower affinity sites is responsible for the non-linear Scatchard plots as well as for the formation of progressively larger complexes between rev and RRE RNA as rev concentrations are increased. When rev concentrations are sufficiently high, RNA is packaged into long ribonucleoprotein filaments, which can easily be detected by electron microscopy. Thus, rev binding to the high affinity site within the RRE RNA may be considered to be the nucleation event for an assembly process during which RNA is packaged into filamentous coats. An analogous process occurs in the packaging of the RNA of tobacco mosaic virus (TMV) and other RNA viruses by their coat proteins (98).

Rev recognition of the "bubble" structure involves both the bulged nucleotides and the two adjacent base pairs on each side. All mutations known to abolish rev activity in vivo (51,68,73) are expected to either delete or disrupt the "bubble" sequence. Residues within the "bubble" are highly conserved in different HIV-1 strains, with the exception of U60 which tolerates C or G substitutions (93). Changes at residue 60 are not expected to impair RRE function significantly, since we have shown that the U60 to C substitution produces only a 2-fold reduction in rev binding.

The "bubble" sequence is highly resistant to nuclease cleavage as well as to modification by chemical reagents (92), suggesting that it forms a compact and rigid structure which locally distorts a double-stranded RNA helix. Details of the structure are still unknown, but the "bubble" could perhaps be stabilized by a non-Watson-Crick G:A base pair (99) between G34 and A61, as well as by stacking interactions.

RNAs carrying RRE sequences are efficiently packaged in vitro into rod-like filaments which can extend over many hundreds of nucleotides and coat the entire length of a template RNA molecule. Filament formation is facilitated by the presence of an RRE sequence. However, rev is also able to bind non-specifically to RNA molecules with approximately 20 fold lower affinity (33,34). The non-specific binding of rev allows RNA molecules that do not carry RRE sequences, such as TMV RNA, to be also packaged into filaments in vitro, provided both the rev and RNA concentrations are sufficiently high. The intracellular binding reaction is likely to involve a competition between rev and hnRNP particle proteins, and this may restrict filament formation to the RRE-containing RNAs.

The RNA binding properties of rev strongly suggest that is blocks splicing simply by packaging unspliced RNA transcripts containing the RRE sequence into inaccessible ribonucleoprotein complexes. Confirmation of our proposal will require the isolation of complexes containing rev and viral mRNAs from infected cells. However, there is already indirect evidence in support of an RNA packaging model for rev activity. Rev is able to influence splicing when the RRE is placed either in an intron or in an unspliced exon and when the RRE is placed at various distances from splice sites (46,65). In addition, rev is believed to disrupt spicing in vitro by blocking spliceosome formation (46). Finally, the in vivo activity of rev is believed to be highly concentration dependent because rev-minus viruses can only be rescued by high concentration of transfected rev-expressing plasmids (88).

The packaging model also provides a simple kinetic explanation for the delayed appearance of the virion RNA relative to the 4.3 kb mRNAs, such as the env mRNA (59). Since the RRE sequence is only 535 nucleotides from the splice acceptor sequence for the second exons of the tat and rev genes, only a short rev filament would be needed to block splicing at this site and allow the production of the 4.3 kb mRNAs. Protection of the additional unused splice donor and acceptor sites located between 1.8–2.0 kb towards the 5' end of the virion RNA would require either the formation of longer ribonucleoprotein filaments or the nucleation of filament formation by rev on secondary sites. In either ease, these processes would be expected to be more efficient towards the end of an infectious cycle when intracellular rev protein concentrations might be expected to be maximal.

Although our model implies that the physical properties of rev can account for its biological activity, it is possible that cellular co-factor(s) are also required (89). Mouse cells infected by HIV have a rev-minus phenotype which can be reversed after fusion to human cells (89). However, in these experiments rev protein levels in the different cell lines were not measured, and it is possible that less rev was expressed in the mouse cells than in the human cells. By contrast, rev is functional in Drosphila melanogaster cells (90).

In conclusion we note that the assembly of rev protein on viral mRNAs carrying RRE sequences is a primary event in the HIV life-cycle and threfore constitutes an important target for therapeutic intervention. As described here, small molecules that interfere with rev binding to the "bubble" sequence can be expected to show anti-HIV activity.

TABLE I

Mutagenesis of the rev binding site.

| Mutation | | $K_d$ (nM) | % RNA bound (10 nM rev) |
|---|---|---|---|
| A. Normal rev binding | | | |
| R7 | wild-type | 3 | 50 |
| R33 | wild-type | 3 | 40 |
| R57 | G38: C57 → A: U | 3 | 40 |
| B. Reduced rev binding | | | |
| R35 | ΔG35 | 4 | 35 |
| R50 | G36 → A | 5 | 20 |
| R52 | U60 → C | 5 | 18 |
| R39 | U33: A63 → A: U | 8 | 15 |
| R54 | U33: A63 → C: G | 6 | 17 |
| R55 | G34: C62 → A: U | 4 | 21 |
| R42 | G38: C57 → C: G | 8 | 18 |
| C. Non-specific rev binding | | | |
| R49 | ΔG59 | — | 2 |
| R45 | ΔU60 | — | 6 |
| R46 | ΔA61 | — | 1 |
| R34 | ΔG35-G36 | — | 3 |
| R36 | ΔG59-A61 | — | 4 |
| R58 | G59 → A | — | 6 |
| R53 | A61 → G | — | 5 |
| R37 | G34, G35, G36 → A, A, A; C62 → U | — | 5 |
| R47 | G35 → A | — | 6 |
| R40 | G34: C62 → C: G | — | 3 |
| R56 | C37: G58 → U: A | — | 6 |
| R41 | C37: G58 → G: C | — | 2 |

Filter binding assays contained 20 pg uniformly labelled RNA probe (500 dpm per pg RNA), 1 μg salmon sperm DNA, 0.45 μg yeast tRNA and 40 units RNasin (Promega) in 500 μl buffer containing 43 mM Tris-HCl pH 8.0, 50 mM KCl. Mutations in the purine-rich "bubble" sequence (numbered as shown in FIG. 2) were introduced into the R33 stem-loop structure (FIG. 3d) by site-directed mutagenesis.

REFERENCES

1. Dayton, A. I., Sodroski, J. G., Rosen, C. A., Goh, W. C. & Haseltine, W. A. Cell 44, 941–947 (1986). (The trans-activator gene of human T cell lymphotropic virus type III is required for replication).
2. Rosen, C. A., Sodroski, J. G., Goh, W. C., Dayton, A. I., Loppke J., 7 Haseltine, W. A. Nature 319, 555–559 (1986).
3. Fisher, A. G., Feinberg, M. B., Josephs, S. F., Harper, M. E., Marselle, L. M., Reyes, G., Gonda, M. A., Aldovini, A., Debouck, C., Gallo, R. C., & Wong-Staal, F. Nature 320, 367–371 (1986). (The trans-activator gene of HTLV-III is essential for virus replication).
4. Hauber, J., Perkins, A., Heimer, E. P., & Cullen, B. R. Proc. Natl. Acad. Sci. USA 84, 6364–6368 (1987).
5. Muesing, M. A., Smith, D. H. & Capon, D. J. Cell 48, 691–701 (1987). (Regulation of mRNA accumulation by a human immunodeficiency virus trans-activator protein).
6. Dingwall, C., Ernberg, I., Gait, M. J., Green, S. M., Heaphy, S., Karn, J., Lowe, A. D., Singh, M., Skinner, M. A., & Valerio, R. Proc. Natl. Acad. Sci. U.S.A. 86, 6925–6929 (1989). (Human immunodeficiency virus 1 tat protein binds trans-activation-responsive region (TAR) RNA in vitro).
7. Muller, W. E. G., Okamoto, T., Reuter, P., Ugarkovic, D., & Schroder, H. C. J. Biol. Chem. 265, 3803–3808 (1990).
8. Guyader, M., Emerman, M., Sonigo, P., Clavel, F., Montagnier, L. & Alizon, M. Nature 326, 662–669 (1987). (Genome organization and trans-activation of the human immunodeficiency virus type 2).
9. Emerman, M., Guyader, M., Montagnier, L., Baltimore, D. & Muesing, M. A. EMBO J. 6, 3755–3760 (1987). (The specificity of the human immunodeficiency virus type 2 transactivator is different from that of human immunodeficiency virus type 1).
10. Roy, S., Parkin, N. T., Rosen, C. A., Itovitch, J. & Sonenberg, N. J. Virol. 64, 1402–1406 (1990). (Structural requirements for trans activation of human immunodeficiency virus type 1 long terminal repeat-directed gene expression by tat: Importance of base-pairing, loop sequences and bulges in the tat-responsive sequence).
11. Berkout, B. & Jeang, K-T. J. Virol. 63, 5501–5504 (1989). (Trans activation of human immunodeficiency virus type 1 is sequence specific for both the single-stranded bulge and loop of the trans-acting responsive hairpin: A quantitative analysis).
12. Selby, M. J., Bain, E. S., Luciw, P. & Peterlin, B. M. Genes Dev.3, 547–558 (1989). (Structure, sequence and position of the stem-loop in tar determine transcriptional elongation by tat through the HIV-1 long terminal repeat).
13. Hauber, J. & Cullen, B. R. J. Virol. 62, 673–679 (1988). (Mutational analysis of the trans-activation responsive region of human immunodeficiency virus type 1 long terminal repeat).
14. Jakobovits, A., Smith, D. H., Jakobovits, E. B. & Capon, D. J. Mol. Cell Biol. 8, 2555–2561 (1988). (A discrete element 3' of human immunodeficiency virus 1 (HIV-1) and HIV-2 mRNA initiation sites mediates transcriptional activation by an HIV trans activator).
15. Peterlin, B. M., Luciw, P. A., Barr, P. J., & Walker, M. D. Proc. Natl. Acad. Sci. U.S.A. 83, 9734–9738 (1986).

16. Berkhout, B., Silverman, R. H. & Jeang, K.-T. Cell 59, 273–282 (1989). (Tat trans-activates the human immunodeficiency virus through a nascent RNA target).
17. Sharp, P. A. & Marciniak, R. A. Cell 59, 229–230 (1989).
18. Jakobovits, A., Rosenthal, A. & Capon, D. J. EMBO J. 9, 1165–1170 (1990).
19. Cullen, B. R. Cell 46, 973–982 (1986).
20. Berkhout, B., Gatignol, A., Silver, J., & Jeang, K.-T. Nucl. Acids. Res. 18, 1839–1846 (1990).
21. Parkin, N. T., Cohen, E. A., Darveau, A., Rosen, C., Haseltine, W., & Sonnenberg, N. EMBO J. 7, 2831–2837 (1988).
22. Edery, I., Petryshyn, R., & Sonnenberg, N. Cell 56, 303–312 (1988).
23. Rice, A. P., & Matthews, M. B. Nature 332, 551–553 (1988).
24. Braddock, M., Chambers, A., Wilson, W., Esnouf, M. P., Adams, S. E., Kingsman, A. J., & Kingsman, S. M. Cell 58, 269–279 (1989).
25. Fenrick, R., Malim, M. H., Hauber, J., Lee, S.-Y., Maizel, J. & Cullen, B. R. J. Virol. 63, 5006–5012 (1989).
26. Morris, C. E., Klement, J. F. & McAllister W. T. Gene 41, 192–200 (1986).
27. Feng, S. & Holland, E. C. Nature 334, 165–168 (1988). (Hiv-1 tat trans-activation requires the loop sequence within TAR).
28. Garcia, J. A., Harrich, D., Soultanakis, E., Wu, F., Mitsuyasu, R. & Gaynor, R. B. EMBO J. 8, 765–778 (1989). (Human immunodeficiency virus type 1 LTR TATA and TAR region sequences required for transcriptional regulation).
29. Adachi, A., Gendelman, H. E., Koenig, S., Folks, T., Willey, R., Rabson, A. & Martin, M. E. J. Virol. 59, 284–291 (1986).
30. Gorman, C. M., Padmanabliam, R. & Howard, B. H. Science 222, 551–553 (1983).
31. Gorman, C. M., Moffat, L. F. & Howard, B. H. Mol. Cell Biol. 2, 1044–1051 (1982).
32. Wu, H.-N. & Uhlenbeck, O. C. Biochemistry, 26, 8221–8227 (1987).
33. Heaphy, S., Dingwall, C., Ernberg, I., Gait, M. J., Green, S. M., Karn, J., Lowe, A. D., Singh, M. and Skinner, M. Cell, 60, 685–693 (1990). (HIV-1 regulator of virion expression (rev) protein binds to an RNA stem-loop structure located within the rev-response element region).
34. Daly, T. J., Cook, K. S., Gary, G. S., Maione, T. E. & Rusche, J. R. Nature, 342, 816–819 (1989). (Specific binding of HIV-1 recombinant rev protein to the rev-responsive element in vitro).
35. Leibold, E. A., Laundano, A., & Yu, Y. Nucl. Acids Res. 18. 1819–1825 (1990).
36. Gaynor, R., Soultanakis, E., Kuwabara, M., Garcia, J., & Sigman, D. S. Proc. Natl. Acad. Sci. U.S.A. 86, 4858–4862 (1989).
37. Gatignol. A., Kumar, A., Rabson, A., & Jaeng K.-T. Proc. Natl. Acad. Sci. U.S.A. 86, 7828–7832 (1989).
38. Kao, S.-Y., Calman, A. F., Luciw, P. A. & Peterlin, B. M. Nature 330, 489–493 (1987). (Anti-termination of transcription within the long terminal repeat of HIV-1 by tat gene product).
39. Toohey, M. G. & Jones, K. A. Genes Dev. 3, 265–283 (1989).
40. Laspia, M. F., Rice, A. P. & Matthews, M. B. Cell 59, 283–292 (1989). (HIV-1 tat protein increases transcriptional initiation and stabilizes elongation).
41. Barik, S., Ghosh, B., Whalen, W., Lazinski, D., & Das, A. Cell 50, 885–899. (1987).
42. Lazinski, D., Grzadzielska, E. & Das, A. Cell 59, 207–218 (1989).
43. Gottesman, M. E., Adhya, S., & Das, A. J. Mol. Biol. 140, 57–75 (1980).
44. Agrawal, S., Goodchild, J., Civiera, M. P., Thornton, A. H., Sarin, P. S. and Zamecnik, P. C. (1988), Proc. Natl. Acad. Sci. U.S.A. 85, 7079–7083.
45. Brill, W. K.-D., Tang, J-Y., Ma, Y-X. and Caruthers, M. H. (1989), J. Amer. Chem. Soc., 111, 2321–2322.
46. Chang, D. A. and Sharp, P. A. (1989) Cell 59, 789–795). (Regulation by HIV rev depends upon recognition of splice site).
47. Cohrane, A. W., Chen, C.-H. and Rosen, C. A. (1990) Proc. Natl. Acad. Sci (USA) 87, 1198–1202. (Specific interaction of the human immunodeficiency virus rev protein with a structured region in the env mRNA).
48. Connolly, B. A., and Newman, P. C., (1989) Nucleic Acids Res., 17, 4957–4974.
49. Cosstick, R. and Vyle, J. S. (1989) Tetrahedron Letters, 30, 4693–4696.
50. Cullen, B. R., Huber, J., Campbell, K., Sodroski, J. G., Haseltine, W. A. and Rosen C. A. (1988) J. Virol. 62, 2498–2501. (Subcellular location of the human immunodeficiency virus trans-acting art gene product).
51. Dayton, E. T., Powell, D. M. and Dayton, A. I. (1989) Science 246, 1625–1629. (Functional analysis of CAR, the target sequence for the rev protein of HIV-1).
52. Emerman, M., Vazeaux, R. and Peden, K. (1989)Cell 57, 1155–1165. (The rev gene product of the human immunodeficiency virus affects envelope specific RNA localization).
53. Feinberg, M. B., Jarrett, R. F., Aldovini, A., Gallo, R. C. and Wong-Stall, F. (1986). Cell 46, 807–817. (HTLV-III expression and production involve complex regulation at the levels of splicing and translation of viral RNA).
54. Felber, B. K., Hadzopoulou-Cladaras, M., Cladaras, C., Copeland, T. and Pavlakis, G. N. (1989). Proc. Natl. Acad. Sci. (USA) 86, 1495–1499). (Rev protein of human immunodeficiency virus type 1 affects the stability and transport of the viral mRNA).
55. Gait, M. J., Jones, A. S. and Walker, R. T. (1974) J. Chem. Soc. Perkin I, 1684–1686.
56. Gait, M. J., Jones, A. S., Jones, M. D., Shepherd, M. J. and Walker, R. T. (1979) J. Chem. Soc. Perkin I, 1389–1394.
57. Helene, C., Montenay-Garestier, T., Saison, T., Takasugi, M., Toulme, J. J., Asseline, U., Lancelot, G., Maurizot, J. C., Toulme, F. and Thuong, N. T. (1985) Biochimie, 67, 777–783.
58. Jones, A. S., (1979) Int. J. Biolog. macromolecules, 1, 194–207.
59. Kim, S., Byrn, R., Groopman, J. and Baltimore, D. (1989) J. Virol. 63, 3708–3713. (Temporal aspects of DNA and RNA synthesis during human immunodeficiency virus infection: Evidence for differential gene expression).
60. Knight, D. M., Flomerfelt, F. A. and Ghrayeb, J. (1987) Science 236, 837–840 (Expression of the art/trs protein of HIV and study of its role in viral envelope synthesis).
61. Krug, A., Oretyskaya, T. S., Volkov, E. M., Cech, D., Shabarova, Z. A. and Rosenthal, A. (1989) Nucleosides and Nucleotides, 8, 1473–1483.
62. Lemaitre, M., Bayard, B. and Lebleu, B. (1987) Proc. Natl. Acad. Sci, USA, 84, 648–652.
63. Letsinger, R. L., Zhang, G., Sun, D. K., Ikeuchi, T. and Sarin, P. (1989) Proc. Natl. Acad. Sci. USA, 86, 6553–6556.

64. Mag, M. and Engels, J. W. (1988) Nucleic Acids Res., 16, 3525–3543.
65. Malim, M. H., Hauber, J., Le, S.-Y., Maizel, J. V. and Cullen, B. R. (1989a) Nature (London) 338, 254–257. (The HIV-1 rev trans-activator acts through a structured target sequence to activate nuclear export of unspliced viral mRNA.
66. Malim, M. H., Bohnlein, S., Fenrick, R., Le, S.-Y. Maizel, J. V. and Cullen, B. R. (1989b) Proc. Natl. Acad. Sci. (USA) 86, 8222–8226. (Functional comparison of the rev trans-activators encoded by different primate immunodeficiency virus species).
67. Malim, M. H., Bohnlein, S., Hauber, J. and Cullen, B. R. (1989c) Cell 58, 205–214. (Functional dissection of the HIV-1 rev trans-activator: Derivation of a trans-dominant repressor of rev function).
68. Malim, M. H., Tiley, L. S., McCarn, D. F., Rusche, J. R., Hauber, J. and Cullen, B. R. (1990) cell 60, 675–683. (HIV-1 structural gene expression requires binding of the rev trans-activator to its RNA target sequence).
69. Miller, P. S., Dreon, N., Pulford, S. M. and McParland, K. B. (1980) J.Biol. Chem., 255, 9569–9665.
70. Miller, P. S., Chandrasegaran, S., Dow, D. L., Pulford, S. M. and Kim, L. S. (1982) Biochemistry, 21, 5468–5474.
71. Miller, P. S., Blake, K. R., Cushman, C. D., Kean, J. M., Lee, B. L., Lin, S-B, and Murakami, A. (1988) Nucleic Acids Res. Special Pub. No. 20, 113–114.
72. Morvan, F., Rayner, B., Inbach, J. L., Thenet. S., Bertrand, J. R., Paoletti, J., Malvy, C. and Paoletti, C. (1987) Nucleic Acids Res., 15, 3421–3437.
73. Olsen, H. S., Nelbrock, P., Cohrane, A. W., Rosen, C. A. (1990) Science 247, 845–848. (Secondary structure is the major determinant for interaction of HIV rev protein with RNA).
74. Perrouault, L., Asseline, U., Rivalle, C., Thuong, N. T., Bisagni, E., Giovannangeli, C., Le Doan, T. and Helene, C. (1990) Nature 344, 358–360.
75. Piccirilli, J. A., Krauch, T., Moroney, S. E. and Benner, S. A. (1990) Nature, 343, 33–37.
76. Rimsky, L., Hauber, J., Dukovich, M., Malim, M. H., Langlois, A., Cullen, B. R. and Greene, W. C. (1988) Nature (London) 335, 738–740. (Functional replacement of the HIV-1 rev protein by the HTLV-1 rex protein).
77. Rosen, C. R., Terwilliger, E., Dayton, A. I., Sodrowski, J. G. and Haseltine, W. A. (1988) Proc. Natl. Acad. Sci. (USA) 85, 2071–2075. (Intragenic cis-acting responsive sequences of the human immunodeficiency virus).
78. Sadaie, M. R., Benter, T. and Wong-Staal, F. (1988) Science 239, 910–913. (Site directed mutagenesis of two trans-regulatory genes (tat-III, trs) of HIV-1).
79. Sodrowski, J., Goh, W. C., Rosen, C. A., Dayton, A., Terwilliger, E. and Haseltine, W. A. (1986) Nature (London) 321, 412–417. (A second post-transcriptional activator gene required for HTLV-III replication).
80. Sproat, B. S., Lamond, A. I., Beijer, B., Neuner, P. and Ryder, U. (1989) Nucleic Acids Res., 17, 3373–3386.
81. Stein, C. A., Subasinghe, C., Shinozuka, K, and Cohen, J. S. (1988) Nucleic Acids Res., 15, 3209–3221.
82. Sun, J-S., Francois, J-C., Lavery, R., Saison-Behmoaras, T., Montenay-Garestier, T., Thuong, N. T. and Helene, C. (1988) Biochemistry, 27, 6039–6045.
83. Vlassov, V. V., Gaidamakov, S. A., Zarytova, V. F., Knorre, D. G., Levina, A. S., Nikonova, A. A. Podust, L. M. and Fedorova, O. S. (1988) Gene, 72, 313–322.
84. Zapp, M. L. and Green, M. R. (1989) Nature (London) 342, 714–716. (Sequence-specific binding by the HIV-1 rev protein).
85. Arrigo S J, Wietsman S, Zack J A, Chen I S Y. Characterization and expression of novel singly spliced RNA species of human immunodeficiency virus type 1. J. Virol. 1990, 64:4585–4588.
86. Schwartz S, Felber B K, Benko D M, Fenyo E-M, Pavlakis G N. Cloning and functional analysis of multiply spliced mRNA species of human immunodeficiency virus type 1. J. Virol. 1990, 64:2519–2529.
87. Heaphy S, Finch J T, Gait M J, Karn J, Singh M. HIV-1 regulator of virion expression, rev, forms nucleoprotein filaments after binding to a purine-rich "bubble" located within the rev-responsive region of viral RNA. Proc. Natl. Acad. Sci. USA 1991, 88:7366–7370.
88. Pomerantz R J, Trono D, Feinberg M B, Baltimore D. Cells nonproductively infected with HIV-1 exhibit an aberrant pattern of viral RNA expression: A molecular model for latency. Cell 1990, 61:1271–1276.
89. Trono D, Baltimore D. A human cell factor is essential for HIV-1 rev action. EMBO J. 1990, 12:4155–4160.
90. Ivey-Hoyle M, Rosenberg M. Rev-dependent expression of human immunodeficiency virus type 1 gp160 in Drosophila melanogaster cells. Mol. Cell. Biol. 1990, 10:6152–6159.
91. Venkatesh L K, Chinnadurai G. Mutants in a conserved region near the carboxy-terminus of HIV-1 rev identify functionally important residues and exhibit a dominant negative phenotype. Virology 1990; 178:327–330.
92. Kjems, J., Brown, M., Chang, D. D., & Sharp, P. A. (1991) Proc. Natl. Acad. Sci. USA 88, 683–687.
93. Le, S.-Y., Malim, M. H., Cullen, B. R. & Maizel, J. V. (1990) Nucleic Acids Res. 18, 1613–1623.
94. Zuker, M. (1989) Science 244, 48–52.
95. Dingwall, C., Ernberg, I., Gait, M. J., Green, S. M., Heaphy, S., Karn, J., Lowe, A. D., Singh, M & Skinner, M. A. (1990) EMBO J. 9, 4145–4153.
96. McGhee, J. D. & von Hippel, P. H. (1974) J. Mol. Biol. 86, 469–489.
97. Holland, S. M., Ahmad, N., Maitra, R. K., Wingfield, P. & Venkatesan, S. (1990) J. Virology. 64, 5966–5975.
98. Turner, D. R., McGuigan, C. J. & Butler, P. J. G. (1989) J. Mol. Biol. 209, 407–422.
99. SantaLucia, J. J., Kierzek, R. & Turner, D. H. (1990) Biochemistry 29, 8813–8819.
100. Gait, M. J., Pritchard, C. & Slim, G. (1991) in "Oligonucleotides and analogues: a practical approach", ed Eckstein, F., Oxford University Press pp 25–49.

What is claimed is:

1. An assay for identifying a compound that inhibits the binding of HIV Rev to HIV RRE, comprising contacting a candidate compound with Rev in the presence of an oligonucleotide that binds to HIV Rev protein with an affinity of no more than 8 nM, wherein the sequence of said oligonucleotide is not found in wild type RRE, and wherein said oligonucleotide comprises a purine-rich bubble containing Watson-Crick base-paired and non-base-paired nucleotides; and determining the degree of binding of Rev to said oligonucleotide relative to the binding in the absence of said candidate compound.

2. An assay for identifying a compound that inhibits the binding of HIV Rev to HIV RRE, comprising contacting a candidate compound with Rev in the presence of an oligonucleotide that binds to HIV Rev protein, said oligonucleotide comprising a purine-rich bubble containing Watson-Crick base-paired and non-base-paired nucleotides and said oligonucleotide comprising at least one base pair adjacent to said bubble and not found in wild type RRE, on at least one side of said bubble; and determining the degree of binding of Rev to said oligonucleotide relative to the binding in the absence of said candidate compound.

3. The assay of claim 2 wherein said oligonucleotide comprises at least two adjacent base pairs on at least one side of said bubble.

4. The assay of claim 2 wherein said oligonucleotide comprises at least four adjacent base pairs on at least one side of said bubble.

5. The assay of claim 1 or 2, wherein the sequence of said purine-rich bubble is selected from the group consisting of:

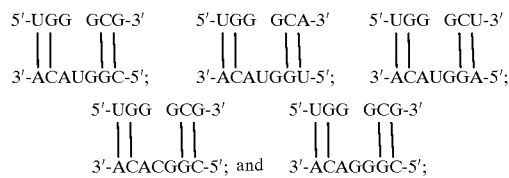

6. The assay of claim 1 or 2, wherein said oligonucleotide comprises one or more 2'-deoxyribonucleotides outside of said purine-rich bubble.

7. An assay for identifying a compound that inhibits the binding of HIV Rev to HIV RRE, comprising contacting a candidate compound with Rev in the presence of a first oligonucleotide and a second oligonucleotide, wherein said first and second oligonucleotides form a duplex that binds to HIV Rev protein with an affinity of no more than 8 nM, and said duplex comprises a purine-rich bubble containing Watson-Crick base-paired and non-base-paired nucleotides; and determining the degree of binding of Rev to said annealed first oligonucleotide and second oligonucleotide relative to the binding in the absence of said candidate compound.

8. An assay for identifying a compound that inhibits the binding of HIV Rev to HIV RRE, comprising contacting a candidate compound with Rev in the presence of a first oligonucleotide and a second oligonucleotide, wherein said first and second oligonucleotides form a duplex that binds to HIV Rev protein and comprises a purine-rich bubble containing Watson-Crick base-paired and non-base-paired nucleotides and said duplex comprises at least one base pair adjacent to said bubble and not found in wild type RRE, on at least one side of said bubble; and determining the degree of binding of Rev to said annealed first oligonucleotide and second oligonucleotide relative to the binding in the absence of said candidate compound.

9. The assay of claim 8, wherein said oligonucleotide comprises at least two adjacent base pairs on at least one side of said bubble.

10. The assay of claim 8, wherein said oligonucleotide comprises at least four adjacent base pairs on at least one side of said bubble.

11. The assay of claim 7 or 8, wherein said first oligonucleotide comprises the sequence 5'-UGGGCG-3' and is annealed to said second oligonucleotide comprising the sequence 5'-CGGUACA-3' to form said purine-rich bubble, which corresponds to

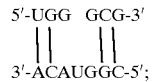

or said first oligonucleotide comprises the sequence 5'-UGGGCA-3' and is annealed to said second oligonucleotide comprising the sequence 5'-UGGUACA-3' to form said purine-rich bubble, which corresponds to

or said first oligonucleotide comprises the sequence 5'-UGGGCU-3' and is annealed to said second oligonucleotide comprising the sequence 5'-AGGUACA-3' to form said purine-rich bubble, which corresponds to

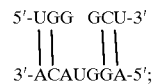

or said first oligonucleotide comprises the sequence 5'-UGGGCG-3' and is annealed to said second oligonucleotide comprising the sequence 5'-CGGCACA-3' to form said purine-rich bubble, which corresponds to

or said first oligonucleotide comprises the sequence 5'-UGGGCG-3' and is annealed to said second oligonucleotide comprising the sequence 5'-CGGGACA-3' to form said purine-rich bubble, which corresponds to

12. The assay of claim 7 or 8, wherein either said first oligonucleotide or said second oligonucleotide comprises one or more 2'-deoxyribonucleotides outside of said purine-rich bubble.

* * * * *